US012303125B2

(12) United States Patent
Vailhe et al.

(10) Patent No.: US 12,303,125 B2
(45) Date of Patent: May 20, 2025

(54) METHODS, SYSTEMS AND DEVICES FOR STORING SUTURE NEEDLES AND USING ROBOTICS FOR DELIVERING SELECTED SUTURE NEEDLES TO SURGICAL SITES

(71) Applicant: Ethicon, Inc., Somerville, NJ (US)

(72) Inventors: Christophe Vailhe, Hillsborough, NJ (US); Doug Souls, Andover, NJ (US)

(*) Notice: Subject to any disclaimer, the term of this patent is extended or adjusted under 35 U.S.C. 154(b) by 645 days.

(21) Appl. No.: 17/380,157

(22) Filed: Jul. 20, 2021

(65) Prior Publication Data

US 2021/0346017 A1 Nov. 11, 2021

Related U.S. Application Data

(62) Division of application No. 16/282,752, filed on Feb. 22, 2019, now Pat. No. 11,103,237.

(51) Int. Cl.
*A61B 17/06* (2006.01)
*A61B 17/00* (2006.01)
(Continued)

(52) U.S. Cl.
CPC .... *A61B 17/06114* (2013.01); *A61B 17/0482* (2013.01); *A61B 17/06061* (2013.01);
(Continued)

(58) Field of Classification Search
CPC ........ A61B 17/06119; A61B 17/06123; A61B 34/30–77; A61B 2017/0479; A61B 2017/00362; A61B 17/0469–0483
See application file for complete search history.

(56) References Cited

U.S. PATENT DOCUMENTS

| 4,123,125 A | 10/1978 | Andry, III |
| D273,615 S | 4/1984 | Maskrey |

(Continued)

FOREIGN PATENT DOCUMENTS

| CN | 102300507 | 12/2011 |
| CN | 106535780 | 3/2017 |

(Continued)

OTHER PUBLICATIONS

International Search Report issued in corresponding International Application No. PCT/IB2020/051378, mailed on Jun. 19, 2020, 3 pages.

*Primary Examiner* — Kathleen S Holwerda
*Assistant Examiner* — Serenity A Miller
(74) *Attorney, Agent, or Firm* — Amir Bishara

(57) ABSTRACT

A surgical method includes arranging a plurality of suture needle containers in a surgical environment, whereby at least one of the suture needle containers includes a receptacle having a proximal end with an opening and a distal end that is closed by an end wall, a suture needle disposed within the receptacle, and a cover sealing the opening at the proximal end of the receptacle for maintaining a sterile environment for the suture needle inside the receptacle. The method includes causing a controller of a surgical robotic system to transmit input instructions to an electromechanical tool for breaching the cover for providing access to the suture needle disposed within the receptacle. After breaching the cover, a distal end of a surgical tool secures the suture needle for removing the secured suture needle from the opening at the proximal end of the receptacle.

17 Claims, 22 Drawing Sheets

(51) Int. Cl.
  *A61B 17/04*      (2006.01)
  *A61B 17/062*     (2006.01)
  *A61B 17/34*      (2006.01)
  *A61B 34/30*      (2016.01)

(52) U.S. Cl.
  CPC ...... *A61B 17/06066* (2013.01); *A61B 17/062* (2013.01); *A61B 17/3478* (2013.01); *A61B 34/30* (2016.02); *A61B 2017/00862* (2013.01); *A61B 17/0493* (2013.01); *A61B 2017/0608* (2013.01); *A61B 2017/06095* (2013.01); *A61B 17/3494* (2013.01)

(56) References Cited

U.S. PATENT DOCUMENTS

| | | |
|---|---|---|
| 5,249,673 A | 10/1993 | Sinn |
| 5,282,533 A | 2/1994 | Holzwarth et al. |
| 5,503,266 A * | 4/1996 | Kalbfeld .......... A61B 17/06133 206/380 |
| 5,655,652 A | 8/1997 | Sobel et al. |
| 5,669,490 A | 9/1997 | Colligan et al. |
| 5,788,062 A | 8/1998 | Cerwin et al. |
| 5,848,714 A | 12/1998 | Robson et al. |
| 5,878,193 A | 3/1999 | Wang et al. |
| 5,906,273 A | 5/1999 | Pohle et al. |
| 6,132,368 A | 10/2000 | Cooper |
| 6,260,696 B1 | 7/2001 | Braginsky |
| 6,530,479 B2 | 3/2003 | Hernandez |
| D568,494 S | 5/2008 | Koseki |
| D569,525 S | 5/2008 | Koseki |
| 7,524,320 B2 | 4/2009 | Tierney et al. |
| 8,177,063 B1 | 5/2012 | Simm et al. |
| 8,418,851 B2 | 4/2013 | Culligan et al. |
| 9,125,662 B2 | 9/2015 | Shelton, IV |
| 9,706,989 B2 | 7/2017 | Lee |
| 2003/0083695 A1 | 5/2003 | Morris et al. |
| 2003/0212417 A1 * | 11/2003 | Rudnick ................ A61B 10/02 606/139 |
| 2010/0084294 A1 | 4/2010 | Kirsch et al. |
| 2010/0230300 A1 | 9/2010 | Hunter et al. |
| 2012/0055828 A1 * | 3/2012 | Kennedy .......... A61B 17/06133 206/363 |
| 2012/0123472 A1 * | 5/2012 | Culligan .......... A61B 17/06114 606/224 |
| 2014/0039527 A1 * | 2/2014 | Avelar ................ A61B 34/74 606/144 |
| 2016/0089139 A1 | 3/2016 | Koman et al. |
| 2017/0079638 A1 | 3/2017 | Pereira |
| 2019/0117215 A1 * | 4/2019 | Belman .............. A61B 17/0625 |

FOREIGN PATENT DOCUMENTS

| | | |
|---|---|---|
| CN | 207666627 | 7/2018 |
| EP | 1842494 | 10/2007 |
| EP | 1852071 | 11/2007 |
| GB | 740988 | 11/1955 |
| JP | S4944754 | 11/1974 |
| JP | S59139245 | 8/1984 |
| WO | 2009026060 | 3/2009 |

* cited by examiner

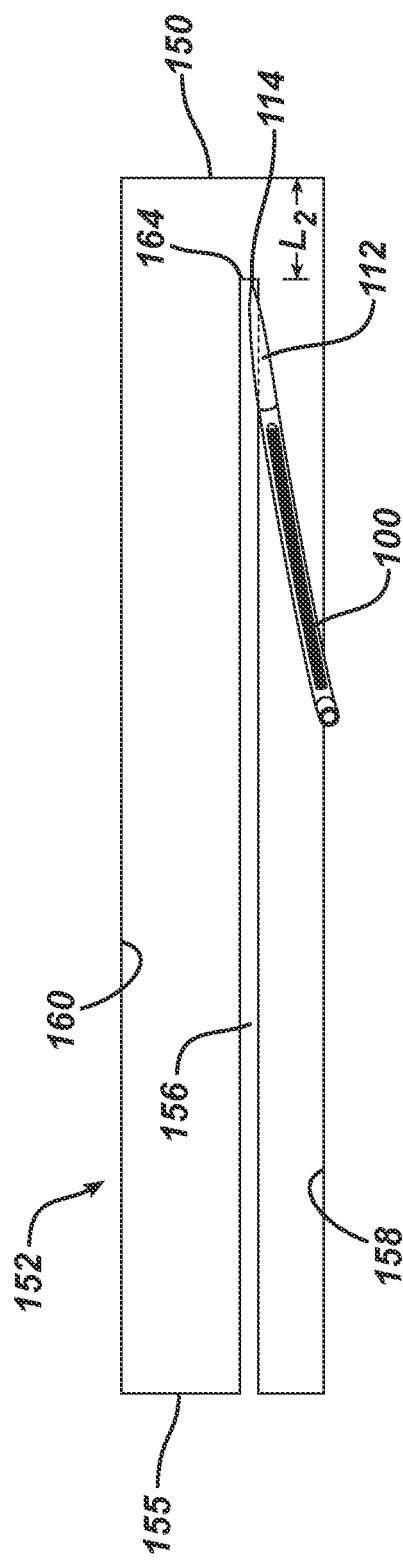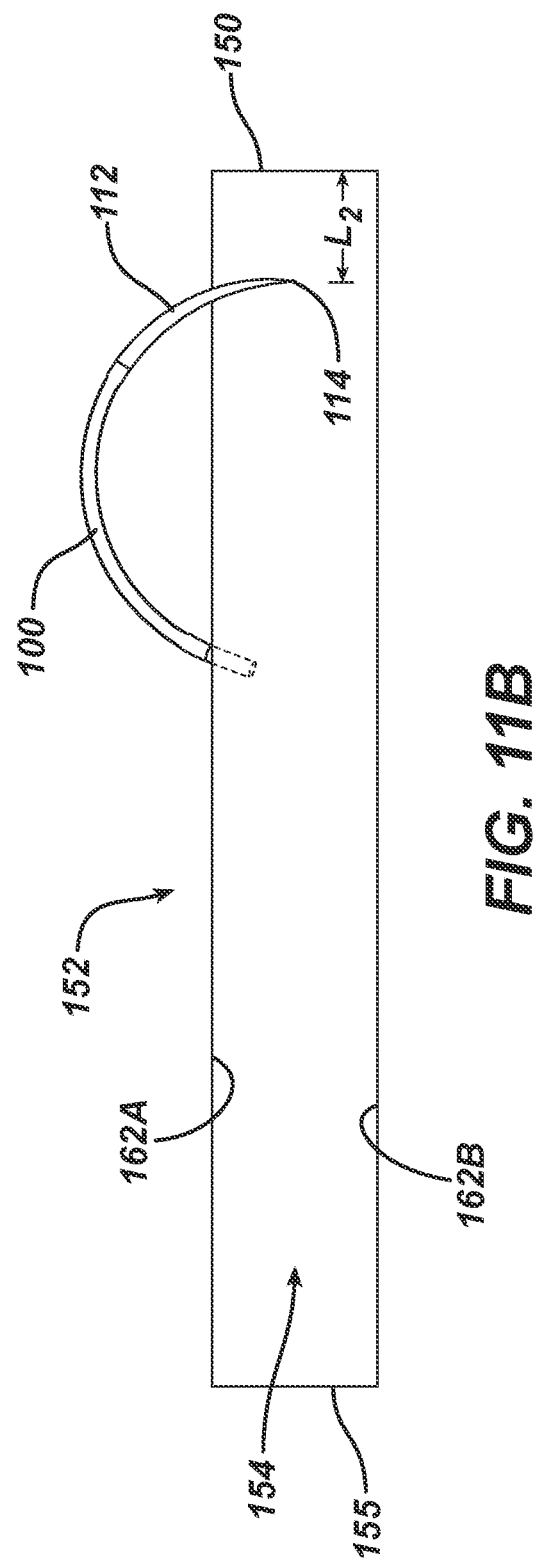

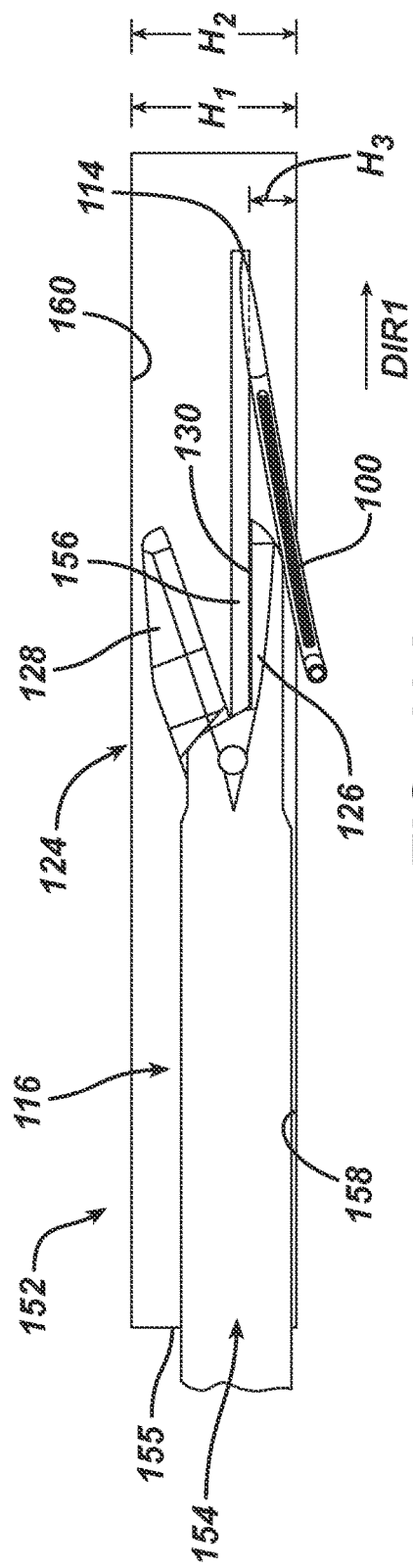
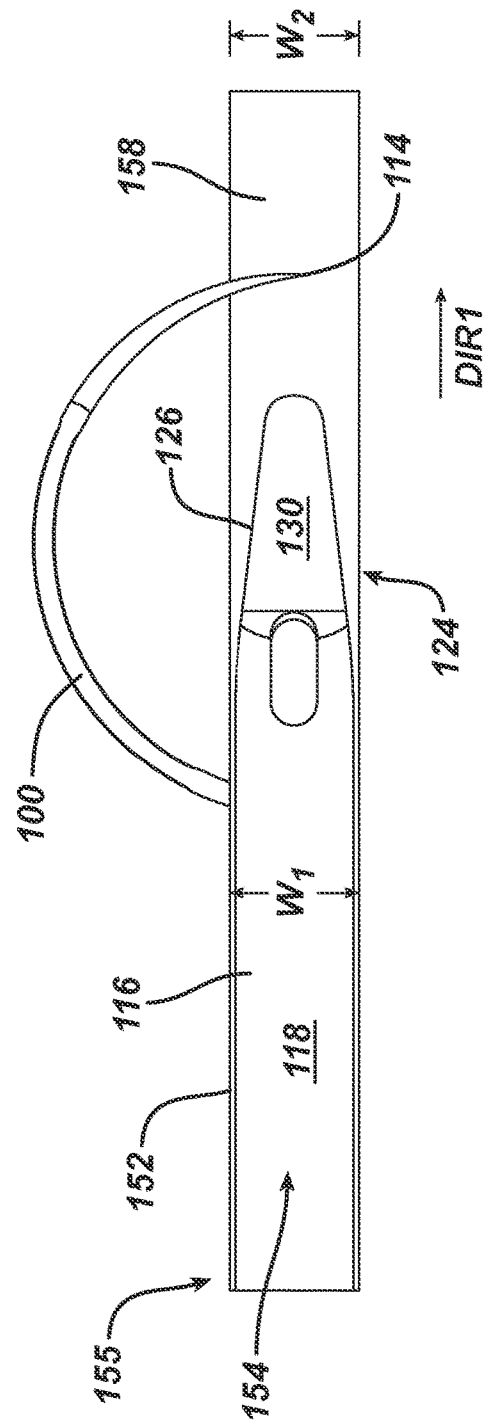
FIG. 12A
FIG. 12B

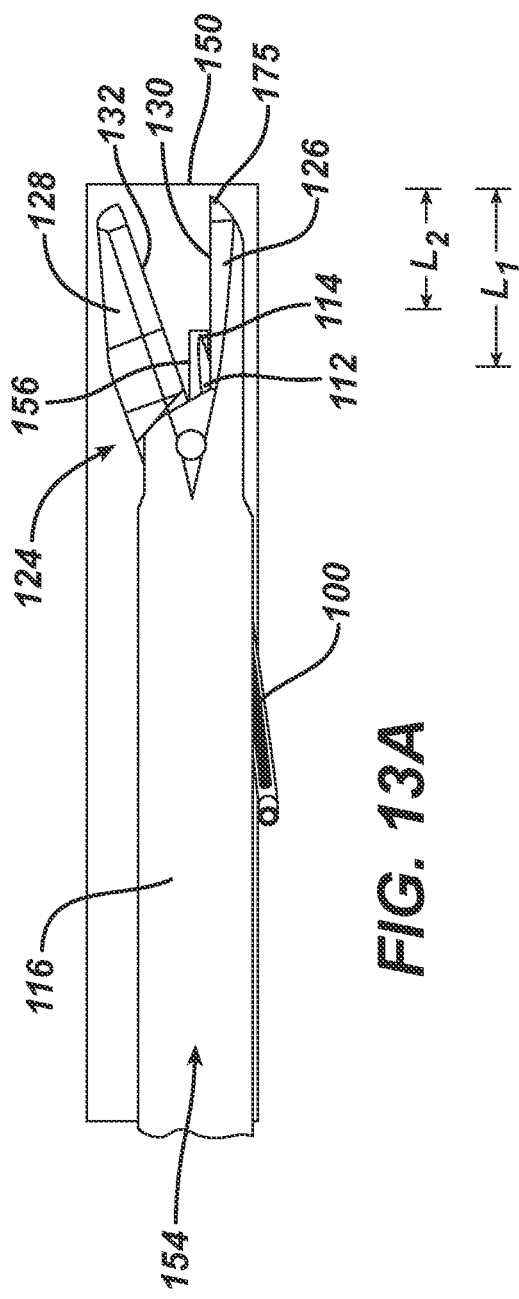
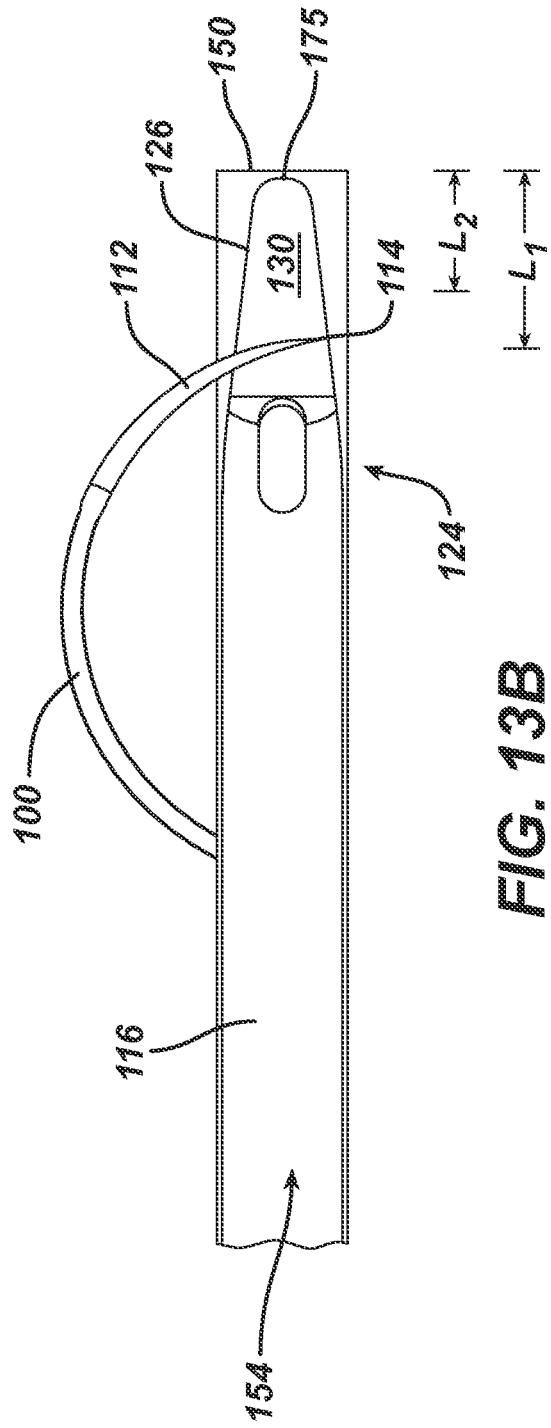
FIG. 13A
FIG. 13B

METHODS, SYSTEMS AND DEVICES FOR STORING SUTURE NEEDLES AND USING ROBOTICS FOR DELIVERING SELECTED SUTURE NEEDLES TO SURGICAL SITES

CROSS-REFERENCE TO RELATED APPLICATIONS

The present patent application is a divisional of U.S. patent application Ser. No. 16/282,752, filed on Feb. 22, 2019, now allowed, the disclosure of which is hereby incorporated by reference herein.

BACKGROUND OF THE INVENTION

Field of the Invention

The present patent application is generally related to surgical systems and tools, and is more specifically related to systems, devices and methods that use robotics for delivering suture needles through trocars during minimally invasive surgery.

Description of the Related Art

Minimally invasive surgical (MIS) instruments and protocols are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, such as suture needles that are used for suturing tissue.

The size of a suture needle (e.g., a needle attached to a suture) or a surgical needle (e.g., a needle that is not attached to a suture) that can be passed through the trocar to a surgical site is often limited by the size of the opening in the trocar. In many instances, surgeons desire to use larger needles for closing surgical wounds and repairing anatomical features, however, passing the larger needles through smaller trocars is difficult. For example, 5 mm trocars are often used during minimally invasive surgeries (MIS), however, surgeons cannot pass the larger suture needles through the 8 mm trocars so they are forced to use only smaller suture needles.

The smaller suture needles are less than optimal because, inter glia, they often require a surgeon to make many more passes of the needle and suture through tissue, which lengthens the surgical procedure and can frustrate the surgeon. Using smaller needles may also produce a bite distance that puts the wound or anatomical feature at risk of dehiscence.

Moreover, larger-sized sutures cannot be easily attached to the smaller suture needles. Thus, when fine sutures are passed through tissue with a smaller bite size, a cheese wire effect may result, whereby the suture cuts through the tissue it is intended to hold.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity and sensitivity of endoscopic tools has been found to be an impediment in the increased use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the fields of minimally invasive surgery and robotic surgery, there remains a need for improved systems, methods and devices for enabling surgeons to select from a range of available suture needles having different properties and performance characteristics and using automated systems, such as robotics, for advancing the selected sutures needles through trocars for being used at surgical sites.

SUMMARY OF THE INVENTION

In one embodiment, a suture needle container preferably includes a receptacle having a proximal end with an opening and a distal end that is closed by an end wall. In one embodiment, the receptacle preferably includes a cylindrical outer wall that extends between the proximal and distal ends of the receptacle. In one embodiment, the receptacle may have a can shape with an open proximal end and a closed distal end.

In one embodiment, a mandrel is located inside the receptacle. In one embodiment, the mandrel has a tubular wall that projects from the end wall of the receptacle toward the opening at the proximal end of the receptacle.

In one embodiment, the tubular wall of the mandrel preferably has a distal end that is connected with the end wall of the receptacle and a proximal end that is in substantial alignment with the proximal end of the receptacle.

In one embodiment, the cylindrical outer wall preferably surrounds the mandrel and the tubular wall of the mandrel is centrally located inside the cylindrical outer wall.

In one embodiment, an elongated slot is desirably formed in the tubular wall of the mandrel that extends from a proximal end of the tubular wall toward the end wall of the receptacle.

In one embodiment, the elongated slot formed in the tubular wall of the mandrel is open at the proximal end of the tubular wall and the elongated slot has a closed end that is proximal to and spaced from the end wall of the receptacle.

In one embodiment, a suture needle is preferably disposed within the elongated slot. The suture needle desirably has a distal end disposed inside the tubular wall of the mandrel and a proximal end disposed outside the tubular wall of the mandrel.

In one embodiment, a suture needle is preferably made of an elastic, hyper-elastic or superelastic material, such as Nitinol. In one embodiment, the suture needle may be elastically deformed to lower the height and/or the profile of the suture needle to pass the suture needle through a trocar, such as a trocar having a diameter of 5 mm or smaller. In one embodiment, an external force may be applied to the suture needle to elastically deform the suture needle (e.g., when passing the suture needle through a trocar), and the suture needle will desirably spring back to its original shape and/or configuration when the external force is removed.

In one embodiment, the suture needle defines a curved element such as an elongated body having a half circle or semi-circle shape. In one embodiment, the suture needle defines ¼ of a circle, ⅜$^{th}$ of a circle, ⅝$^{th}$ of a circle, ¾ of a circle, etc.

In one embodiment, the suture needle may have a bendable region or may be highly elastic for changing shape and/or configuration to fit through a trocar (e.g., a 5 mm trocar), as disclosed in commonly assigned U.S. patent application Ser. No. 16/282,604, filed on Feb. 22, 2019, published as US 2020/0268378, 16/282,652, filed on Feb. 22, 2019, published as US 2020/0268379, and U.S. patent application Ser. No. 16/781,055, filed on Feb. 4, 2020, which claims benefit of U.S. Provisional Application Number 62/809,016, filed on Feb. 22, 2019, and now published as US 2020/0268380, the disclosures of which are hereby incorporated by reference herein.

In one embodiment, a cover preferably seals the opening at the proximal end of the receptacle for maintaining a sterile environment inside the receptacle.

In one embodiment, the distal end of the suture needle preferably includes a tapered section that terminates at a tip that defines a distal-most end of the suture needle. In one embodiment, when the suture needle is held within the elongated slot of the mandrel, the tip of the suture needle is located inside the tubular wall of the mandrel and the tapered section of the suture needle desirably passes through the elongated slot formed in the tubular wall of the mandrel.

In one embodiment, a distal portion of the tapered section of the suture needle is disposed inside the tubular wall of the mandrel and a proximal portion of the suture needle is disposed outside the tubular wall of the mandrel and inside the receptacle.

In one embodiment, the tubular wall of the mandrel preferably defines a needle driver guide channel having a height and a width. In one embodiment, the needle driver guide channel extends from the proximal end of the tubular wall of the mandrel to the distal end of the tubular wall of the mandrel.

In one embodiment, a needle driver may be used for removing a suture needle from the elongated slot of the mandrel. In one embodiment, the needle driver preferably includes an elongated shaft having with a distal end with a clamping assembly having lower and upper jaws moveable between an open position and a closed position. In one embodiment, when the lower and upper jaws are in the open position, the jaws define an open jaw height that matches the height of the needle driver guide channel. In addition, the lower and upper jaws preferably define a jaw width that matches the width of the needle driver guide channel.

In one embodiment, a needle driver may be used to secure a tapered section at a distal end of the suture needle with the barrel of the suture needle trailing behind the tip of the suture needle. In one embodiment, the tip is preferably surrounded by clamping jaws at the distal end of the needle driver for protecting the tip as the suture needle is passed through a trocar. The damping jaws preferably surround and protect the tip for preventing the tip from contacting the inside of the trocar as it is passed through the trocar, which could damage the tip during its passage through the channel of the trocar.

In one embodiment, when the suture needle is held by the needle driver, the tip of the needle does not extend or protrude outside the external surface of the needle holder. In one embodiment, the tapered section of the suture needle preferably extends along an axis that defines an angle with the longitudinal axis of the needle driver alignment channel of less than 90 degrees, which preferably enables the suture needle to be passed through a trocar using less force.

In one embodiment, the needle driver guide channel preferably has a floor located at a lower end of the needle driver guide channel, a ceiling located at an upper end of the needle driver guide channel, and opposing side walls that extend between the floor and the ceiling. In one embodiment, the elongated slot of the mandrel is desirably formed in one of the opposing side walls. In one embodiment, the floor of the needle driver guide channel preferably has a surface (e.g., a concave surface) that conforms to an underside of the elongated shaft of the needle driver (e.g., a cylindrical surface).

In one embodiment, the elongated shaft of the needle driver preferably has an outer diameter, and the elongated slot formed in the mandrel is preferably spaced away from the floor of the needle driver guide channel by a distance that is greater than ½ of the outer diameter of the elongated shaft of the needle driver.

In one embodiment, the lower jaw of the needle driver preferably has a distal end and a top surface, which is adapted to engage the tapered section of the suture needle disposed inside the tubular wall of the mandrel. In one embodiment, the top surface of the lower jaw has a length that is greater than a distance between the closed end of the elongated slot and the end wall of the receptacle. In one embodiment, when the distal end of the lower jaw is abutted against the end wall of the receptacle, the tip of the suture needle is preferably aligned over the top surface of the lower jaw.

In one embodiment, the cover sealing the opening at the proximal end of the receptacle may be made of foil, polymers, plastics, high-density polyethylenes, and/or Tyvek.

In one embodiment, a suture needle container preferably includes a receptacle having a proximal end with an opening and a closed distal end, and a hollow mandrel disposed inside the receptacle. In one embodiment, the mandrel preferably projects from the closed distal end of the receptacle toward the opening at the proximal end of the receptacle.

In one embodiment, the hollow mandrel desirably includes a tubular wall having a proximal end aligned the proximal end of the receptacle and a distal end connected with the closed distal end of the receptacle, and an elongated slot formed in the tubular wall of the hollow mandrel that extends from the proximal end of the tubular wall to a location that is proximal to and spaced from the closed distal end of the receptacle.

In one embodiment, a suture needle may be disposed within the elongated slot. In one embodiment, when the suture needle is held within the elongated slot, the suture needle preferably has a distal end with a tip that is disposed inside the tubular wall of the hollow mandrel and a proximal end disposed outside the tubular wall of the hollow mandrel. In one embodiment, a suture is secured to the proximal end of the suture needle and the suture has a length that is wrapped around the hollow mandrel.

In one embodiment, a cover preferably closes the opening at the proximal end of the receptacle for sealing the suture needle and the suture inside the receptacle and for maintaining a sterile environment inside the receptacle. The cover preferably forms an air-tight seal over the opening of the receptacle.

In one embodiment, the tubular wall of the hollow mandrel preferably defines a needle driver guide channel having a height and a width. In one embodiment, the needle driver guide channel desirably extends from the proximal end of the tubular wall of the hollow mandrel to the distal end of the tubular wall of the hollow mandrel.

In one embodiment, a needle driver may be used for removing a suture needle from a suture needle container. In one embodiment, the needle driver desirably includes an elongated shaft having a distal end with a clamping assembly having lower and upper jaws moveable between open and closed positions.

In one embodiment, the lower and upper jaws in an open position define an open jaw height that matches the height of the needle driver guide channel. In one embodiment, the lower and upper jaws define a jaw width that matches the width of the needle driver guide channel.

In one embodiment, the needle driver guide channel preferably has a floor located at a lower end of the needle driver guide channel, a ceiling located at an upper end of the needle driver guide channel, and opposing side walls that extend between the floor and the ceiling. In one embodiment, the elongated slot is formed in one of the opposing side walls and is closer to the floor than the ceiling of the needle driver guide channel.

In one embodiment, the elongated shaft of the needle driver desirably has an outer diameter. In one embodiment, the elongated slot formed in the tubular wall of the hollow mandrel is preferably spaced away from the floor of the needle driver guide channel by a distance that is greater than ½ of the outer diameter of the elongated shaft of the needle driver.

In one embodiment, the lower jaw preferably has a distal end and a top surface adapted to engage the distal portion of the tapered section of the suture needle disposed inside the tubular wall of the mandrel. In one embodiment, the top surface of the lower jaw has a length that is greater than a distance between the closed end of the elongated slot and the closed distal end of the receptacle, which facilitates consistently aligning the tip of the suture needle over the top surface of the lower jaw when the distal end of the lower jaw is abutted against the closed distal end of the receptacle.

In one embodiment, the distal end of the suture needle may include a tapered section that terminates at the tip, which defines a distal-most end of the suture needle. In one embodiment, when the suture needle is secured within the elongated slot formed in the tubular wall of the mandrel, the tip is desirably located inside the tubular wall of the hollow mandrel and the tapered section of the suture needle preferably passes through the elongated slot.

In one embodiment, a rack assembly that contains a plurality of medical devices used during surgical procedures may be oriented in a substantially planar or vertical configuration. The rack assembly may have a plurality of removably attached medical devices or tools (e.g., end-effectors and/or objects to be used with end-effectors). The location of each of the devices is preferably predetermined and cataloged in a robotic or computer controlled system. When needed, a surgical robotic arm preferably interacts with the computer controlled sytem to locate and retrieve a device (e.g., a suture needle capsule, a suture needle, a needle driver) from the rack.

In one embodiment, the rack may be automated to position a medical device, which is desired to be coupled to a robotic arm, at a known and convenient location.

In one embodiment, one or more of the devices (e.g., suture needle capsules) may be encoded (e.g., bar codes, RFI© chips, etc.) so that the robotic system and robotic arms may determine what the device is and/or confirm that the device is the one it expected to see at the given location. The device may be selected from a wide variety of surgical tools such as suture needle containers, suture needles, sutures, and/or implants. The devices may be enclosed within a sterile container or chamber, whereby the robotic arm may easily pass through a frangible barrier to retrieve the device.

In one embodiment, a surgical method may use robotics for loading a suture needle onto a surgical tool such as a needle driver, removing the loaded suture needle from a suture needle container, and passing the loaded suture needle through a trocar for positioning the suture needle at a surgical site.

In one embodiment, a surgical method preferably includes arranging a plurality of suture needle containers in a surgical environment (e.g., positioning the suture needle containers within a matrix having rows and columns), whereby each suture needle container desirably includes a receptacle having a proximal end with an opening and a distal end that is closed by an end wall, a mandrel located inside the receptacle having a tubular wall that projects from the end wall toward the opening at the proximal end of the receptacle, an elongated slot formed in the tubular wall of the mandrel that extends from a proximal end of the tubular wall toward the end wall of the receptacle, a suture needle disposed within the elongated slot having distal end disposed inside the tubular wall and a proximal end disposed outside the tubular wall, and a cover sealing the opening at the proximal end of the receptacle for maintaining a sterile environment inside the receptacle.

In one embodiment, a surgical method preferably includes after selecting one of the suture needles inside one of the suture needle containers for use, causing a controller on a surgical robotic system to transmit input instructions to an electromechanical tool to breach the cover of the selected one of the suture needle containers, secure the distal end of the selected one of the suture needles, and remove the secured suture needle from the breached suture needle container.

In one embodiment, a surgical method may include causing the controller of the surgical robotic system to transmit input instructions to the electromechanical tool to advance the secured suture needle through a trocar.

In one embodiment, a suture needle container preferably includes a centrally located mandrel having a needle driver guide channel formed therein that has a shape and dimension that engages the outer surface of the distal end of the needle driver for controlling the direction and the angle of the needle holder when loading a suture needle onto the distal end of the needle driver.

In one embodiment, the inside geometry of the needle driver guide channel preferably matches the geometry of the needle holder when the lower and upper jaws at the distal end of the needle holder are in an open position.

In one embodiment, a distal end of the lower jaw of the needle holder abuts against a hard stop for consistently aligning a damping surface of the lower jaw with a distal end of the needle held within the needle driver guide channel.

In one embodiment, the mandrel that defines the needle driver guide channel has an elongated slot formed therein, whereby the suture needle is held in the elongated slot and slides out of the elongated slot for being removed from the suture needle container.

In one embodiment, a suture is secured to the proximal end of the suture needle and is wound around the mandrel when packing the suture needle and the suture inside the suture needle container, Winding the suture around the mandrel preferably facilitates easy removal and/or release of the suture from the suture needle container.

In one embodiment, the suture needle container has an access opening at a proximal end thereof that is sealed with a cover to maintain sterility for the suture needle and suture packed into the suture needle container.

In one embodiment, the suture needle container may be part of a robotic system whereby the suture needle may be automatically loaded onto an end of a tool (e.g., a needle driver) and the loaded suture needle advanced by the system through a trocar for placing the suture needle at a surgical site.

In one embodiment, systems, devices and methods are provided for use in robotic surgery, and in particular for communicating with and controlling robotic tools including end effectors.

In one aspect, a surgical robotic system is provided that includes an electromechanical arm configured for movement in multiple axes and a suture needle securing tool, such as a needle driver having a clamping assembly, configured to couple to the electromechanical arm. In one embodiment, the robotic system preferably includes a controller that is configured to control movement of the electromechanical arm and to control actuation of the clamping assembly of the suture needle securing tool. The electromechanical tool may include at least one visual indicator indicative of a length scale that is effective to allow an action of the end effector to be visually measured. The controller is configured to modify the action of the end effector based on the visually measured action.

In one embodiment, a robotic system may include a controller that transmits instructions input by a surgeon or medical personnel to an electromechanical tool to move the tool. The system may have a pre-set motion control threshold, and the controller may be configured to prevent the electromechanical tool from exceeding the pre-set motion control threshold when the controller moves the tool.

As used herein, the terms surgical needle and suture needle are used interchangeably. A surgical needle may have a suture attached thereto or may not have a suture attached thereto. A suture needle may have a suture attached thereto or may not have a suture attached thereto. Regardless of whether the terms surgical needle or suture needle are used herein, the terms may be used to describe both needles having sutures attached thereto and needles that do not have sutures attached thereto.

These and other preferred embodiments of the present invention will be described in more detail below.

BRIEF DESCRIPTION OF THE DRAWINGS

FIG. 11A shows a cross-sectional side view of a mandrel having a needle driver guide channel for aligning a clamping assembly with a suture needle, in accordance with one embodiment of the present patent application.

FIG. 11B shows a cross-sectional top view of the mandrel shown in FIG. 11A.

FIG. 12A shows a cross-sectional side view of the mandrel of FIG. 11A with a needle driver inserted into a needle driver guide channel, in accordance with one embodiment of the present patent application.

FIG. 12B shows a cross-sectional top view of the mandrel and the needle driver shown in FIG. 12A.

FIG. 13A shows a cross-sectional side view of the mandrel of FIG. 11A with a clamping assembly of a needle driver aligned with a tip of a suture needle, in accordance with one embodiment of the present patent application.

FIG. 13B shows a cross-sectional top view of the mandrel and the needle driver shown in FIG. 13A.

DETAILED DESCRIPTION OF PREFERRED EMBODIMENTS

Figure 1A:
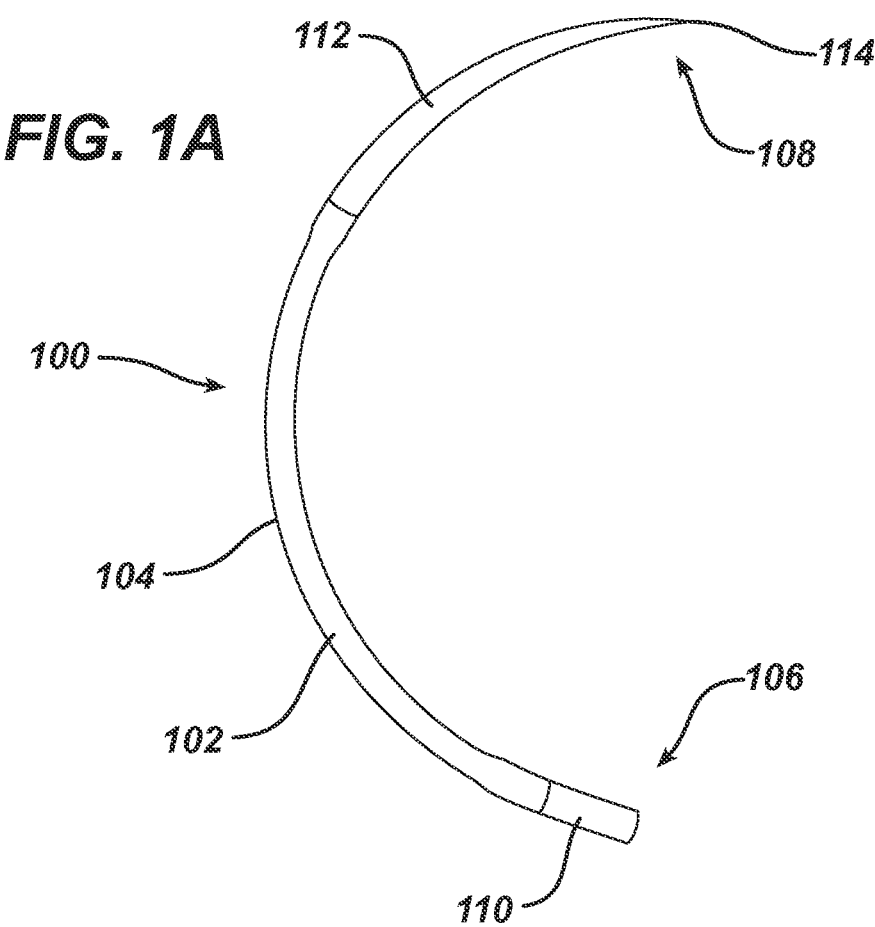
FIG. 1A is a side view of a suture needle having a proximal end and a distal end with a tapered section and a distal tip, in accordance with one embodiment of the present patent application.
Figure 1B:
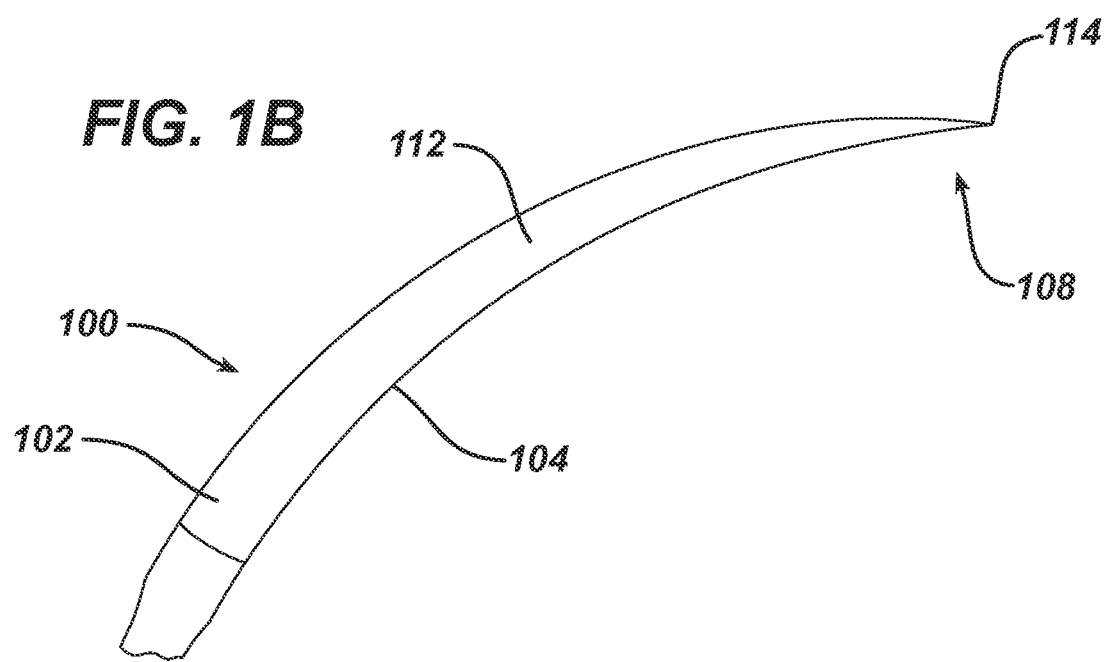
FIG. 1B is a magnified view of the tapered section and the distal tip of the suture needle shown in FIG. 1A.

Referring to FIGS. 1A and 1B, in one embodiment, a suture needle 100 preferably includes an elongated body 102 having an outer surface 104 that extends from a proximal end 106 to a distal end 108 of the suture needle. In one embodiment, the proximal end 106 desirably includes a barrel 110 having a suture attachment opening located at a proximal end face of the suture needle, which is adapted to receive an end of a suture for attaching the suture to the proximal end of the suture needle 100. A distal section of the suture needle 100 preferably includes a tapered section 112 that tapers inwardly to a distal tip 114 (e,g, a sharpened point), which is desirably located at a distal-most end of the suture needle 100. In one embodiment, the suture needle 100 is preferably made of an elastic, hyper-elastic, or superelastic material such as Nitinol, which enables the suture needle to flex from a first shape (e.g., a half circle) to a second shape (e.g., a shape that is flatter than a half circle) for passing the suture needle through a trocar (e.g., a 5 mm trocar). After the suture needle has passed through the trocar, the elastic, hyper-elastic or superelastic suture needle (hereinafter collectively referred to as a "suture needle") will desirably return back to the original half circle shape shown in FIGS. 1A and 1B. In one embodiment, the elastic suture needle 100 has a semi-circular shape. In one embodiment, the elastic suture needle covers $3/8^{th}$ of a circle, $1/2$ of a circle, $5/8^{th}$ of a circle, $3/4$ of a circle, etc.

In one embodiment, the suture needle 100 may have a bendable region or may be highly elastic for changing shape and/or configuration to fit through a trocar (e.g., a 5 mm trocar), as disclosed in commonly assigned U.S. patent application Ser. No. 16/282,604, filed on Feb. 22, 2019, published as US 2020/0268378, U.S. patent application Ser. No. 16/282,652, filed on Feb. 22, 2019, published as US 2020/0268379, and U.S. patent application Ser. No. 16/781,055, filed on Feb. 4, 2020, which claims benefit of U.S. Provisional Application No. 62/809,016, filed on Feb. 22, 2019, and now published as US 2020/0268380, the disclosures of which are hereby incorporated by reference herein.

Figure 2A:
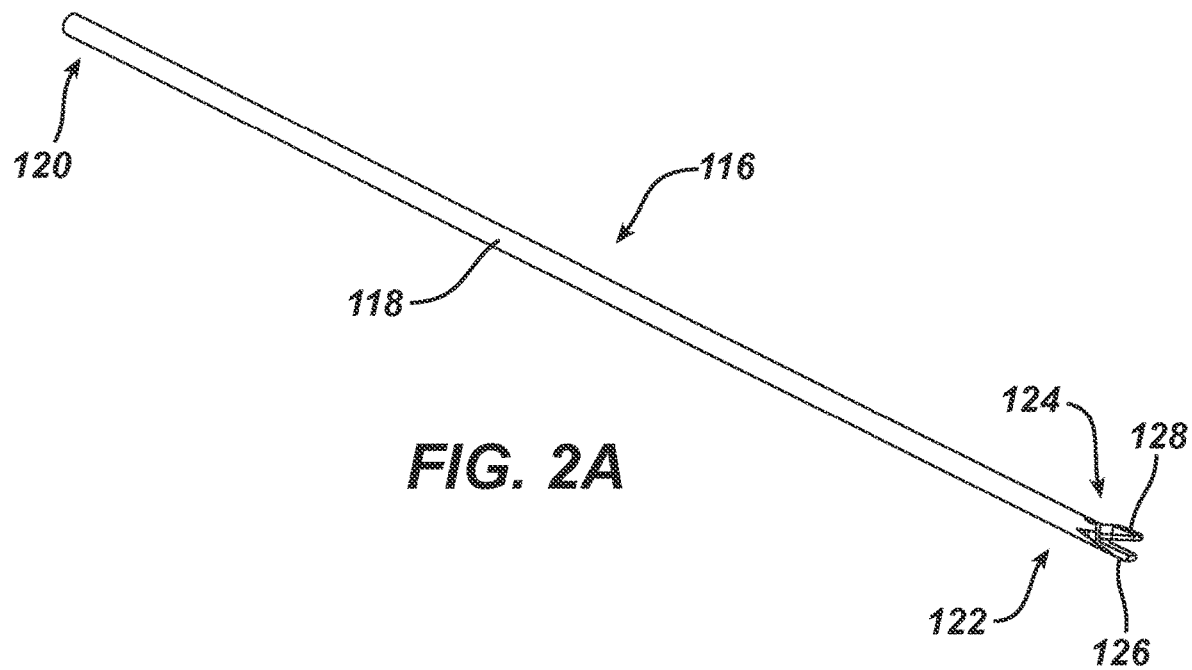
FIG. 2A is a perspective view of a needle driver having an elongated shaft with a proximal end, a distal end, and a clamping assembly at the distal end of the elongated shaft, the clamping assembly including lower and upper jaws moveable between open and closed positions, in accordance with one embodiment of the present patent application.
Figure 2B:
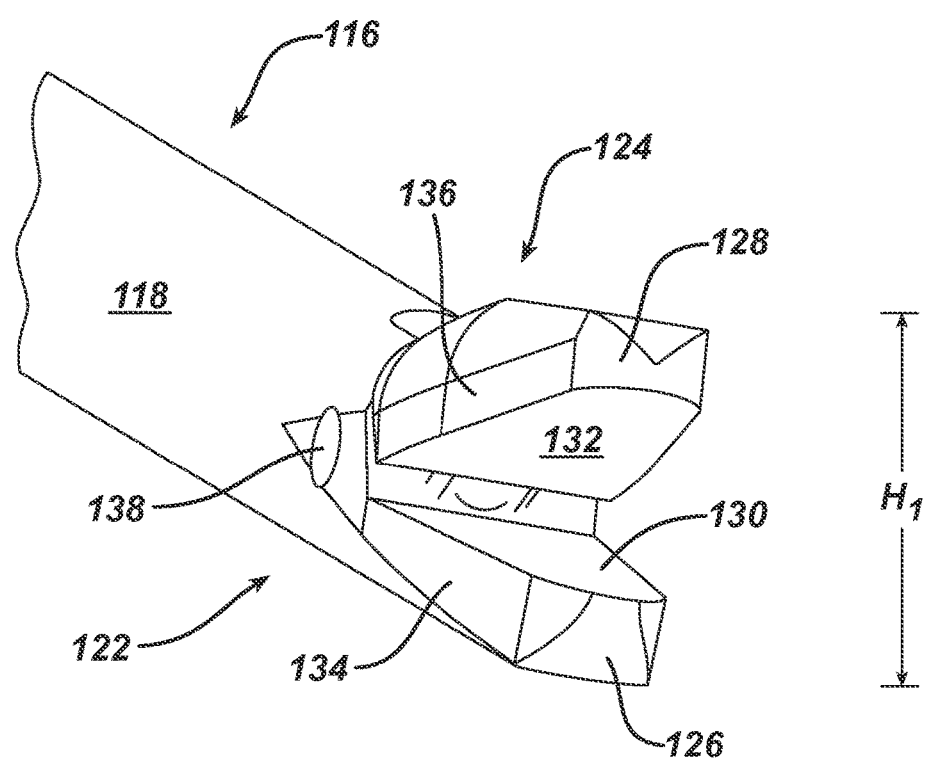
FIG. 2B is a perspective view of the distal end of the elongated shaft and the clamping assembly of the needle driver shown in FIG. 2A.

Referring to FIGS. 2A and 2B, in one embodiment, a needle driver 116 may be utilized for securing the suture needle 100 shown and described above in FIGS. 1A-1B, In one embodiment, the suture needle is preferably releasably secured within a suture needle container for being removed from the container by the needle driver. In one embodiment, the needle driver 116 preferably includes an elongated shaft 118 having a proximal end 120 and a distal end 122 with a clamping assembly 124 provided at the distal end 122 of the elongated shaft 118. In one embodiment, the clamping assembly preferably includes a lower jaw 126 and an upper jaw 128 that opposes the lower jaw. The clamping assembly 124 is preferably movable between an open position for receiving an object between the jaws and a closed position for clamping onto the object positioned between the jaws. In the closed position, the clamping assembly preferably secures elements such as suture needles between the opposing lower and upper jaws 126, 128.

Referring to FIG. 2B, in one embodiment, the lower jaw 126 preferably has a top surface 130 that opposes a bottom surface 132 of the upper jaw 128. In one embodiment, the top and bottom surfaces 130, 132 of the respective lower and upper jaws 126, 128 are preferably mirror images of one another. In one embodiment, one or more of the top and bottom surfaces 130 has a surface roughening such as knurling for gripping the suture needle between the jaws when the clamping assembly is in the closed position. In one embodiment, the lower jaw 126 has a lateral surface 134 that defines the outer perimeter of the top surface 130 of the lower jaw 126. Similarly, the upper jaw 128 has a lateral surface 136 that defines the outer perimeter of the bottom surface 132 of the upper jaw 128. In one embodiment, the lower jaw 126 may be rigidly secured to the distal end 122 of the elongated shaft 118. The upper jaw 128 is preferably pivotally secured to the distal end 122 of the elongated shaft 118 via a pivot 138 that couples a proximal end of the upper jaw 128 to the distal end 122 of the elongated shaft 118. In one embodiment, the pivot 138 desirably enables the upper jaw 128 to pivot relative to the lower jaw 126 for moving the clamping assembly 124 between the open and closed positions.

In one embodiment, when the lower and upper jaws 126, 128 are in the open position (FIG. 2B), the clamping assembly 124 defines a height $H_1$ that extends from the top of the upper jaw 128 to the bottom of the lower jaw 126.

Figure 3A:
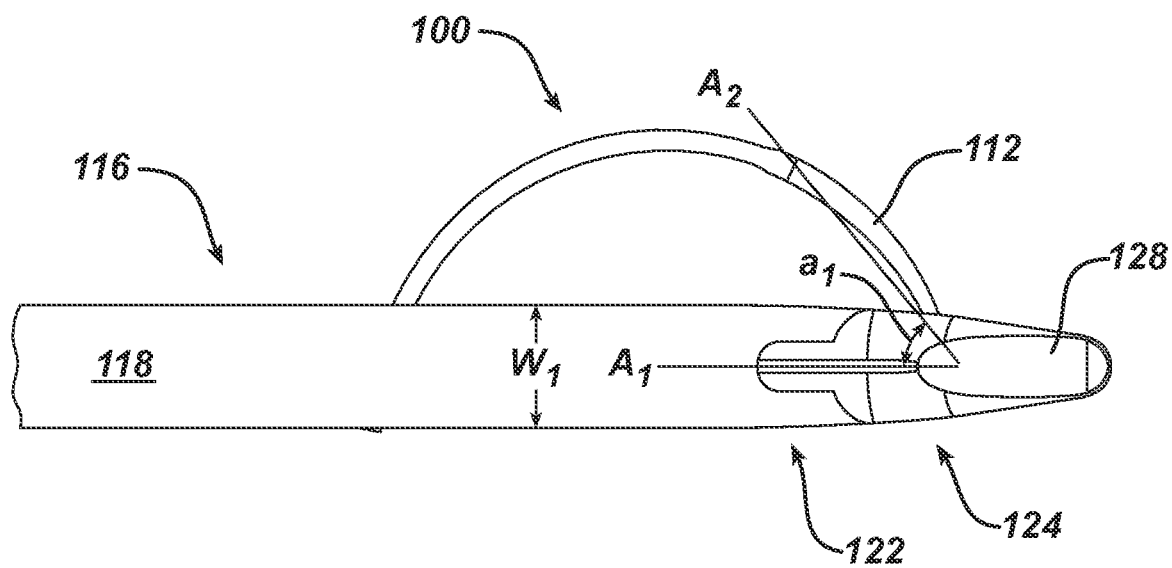
FIG. 3A shows a top plan view of a distal end of a needle driver having a clamping assembly with lower and upper jaws for securing a suture needle, in accordance with one embodiment of the present patent application.

Referring to FIG. 3A, in one embodiment, the elongated shaft 118 of the needle driver preferably has an outer diameter that defines a distance $W_1$.

Figure 3B:
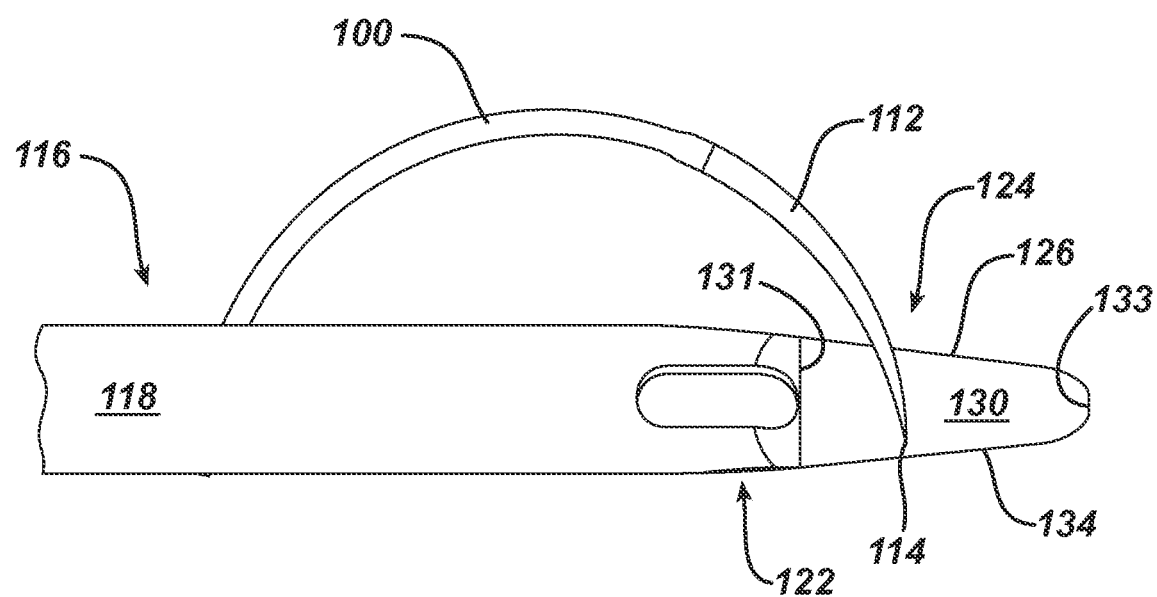
FIG. 3B shows the distal end of the needle driver shown in FIG. 3A with the upper jaw remover.

Referring to FIGS. 3A and 3B, in one embodiment, the clamping assembly 124 at the distal end 122 of the elongated shaft 118 is adapted to secure a distal section of the suture needle 106. In one embodiment, the top and bottom surfaces of the respective lower and upper jaws 126, 128 preferably clamp onto the tapered section 112 of the suture needle and the lower and upper jaws surround the tip 114 of the suture needle so that the tip is not exposed outside the outer perimeters of the top and bottom surfaces of the respective lower and upper jaws 126, 128.

In one embodiment, the elongated shaft 118 of the needle driver 116 preferably extends along a longitudinal axis $A_1$. In one embodiment, when the tapered section 112 of the suture needle 100 is secured between the lower and upper jaws 126, 128, the tapered section 112 of the suture needle 100 preferably extends along a second axis $A_2$ that defines an angle $\alpha_1$ with the longitudinal axis $A_1$ of the elongated shaft 118 that is less than 90°. Positioning the tapered section 112 of the suture needle 100 at an angle $\alpha_1$ of less than 90° relative to the longitudinal axis $A_1$ of the needle driver 116 enables the trailing end of the suture needle to extend proximally toward a proximal end of the needle driver, which will reduce the amount of force required to pass the suture needle through a trocar.

Referring to FIG. 3B, in one embodiment, the top surface 130 of the lower jaw 126 preferably has a proximal end 131 and a distal end 133 that define a length $L_1$ of the top surface. In one embodiment, the top surface 130 of the lower jaw 126 is desirably configured for alignment with the tip 114 of the suture needle 100 with the tip positioned between the proximal and distal ends of the top surface 130 and within the outer perimeter of the top surface. With the tip 114 of the suture needle 100 aligned with the top surface 130 of the lower jaw 126, the tapered section 112 of the suture needle 100 preferably extends over a lateral side 135 of the lower jaw 126 with trailing end of the suture needle extending proximally toward a proximal end of the elongated shaft 118 of the needle driver 116.

Figure 3C:
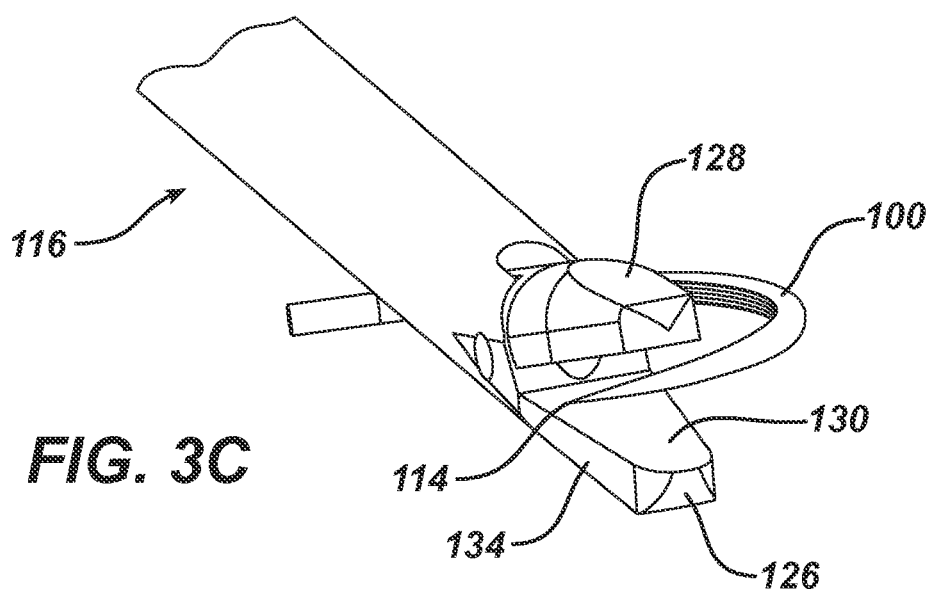
FIG. 3O shows a perspective end view of the distal end of the needle driver shown in FIGS. 3A-3B.
FIG. 3D shows another perspective end view of the needle driver shown in FIGS. 3A-3C.
Figure 3D:
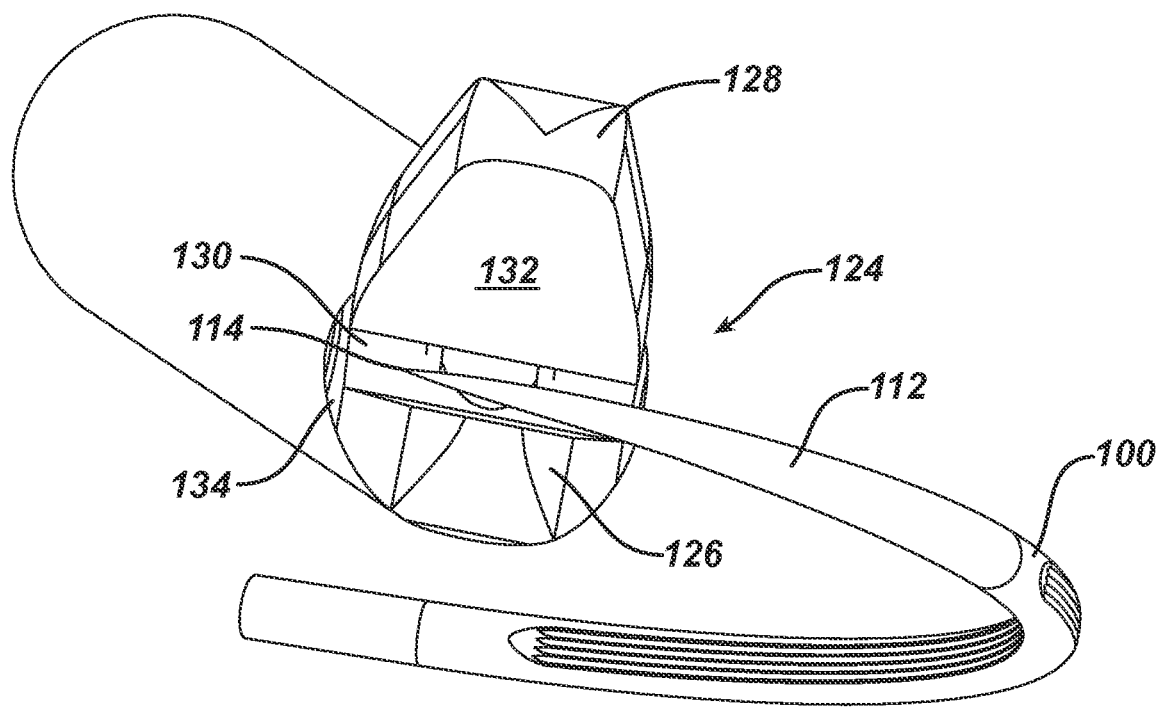

Referring to FIGS. 3C and 3D, in one embodiment, the needle driver 116 is preferably advanced toward the tip 114 of the suture needle 100 so that the tip 114 is positioned between the top surface 130 of the lower jaw 126 and the bottom surface 132 of the upper jaw 128. In one embodiment, the tip 114 is desirably positioned within the outer perimeter of the top surface 130 of the lower jaw 126 so that the tip 114 is not exposed outside the lower jaw.

Referring to FIG. 3D, in one embodiment, when the clamping assembly 124 is closed, the top and bottom surfaces 130, 132 of the respective lower and upper jaws 126, 128 preferably engage the tapered section 112 of the suture needle 100 so that the tip 114 of the suture needle 100 is not contacted, pinched, compressed, and/or deformed by the lower and upper jaws when the lower and upper jaws move into the closed position.

Figure 4A:
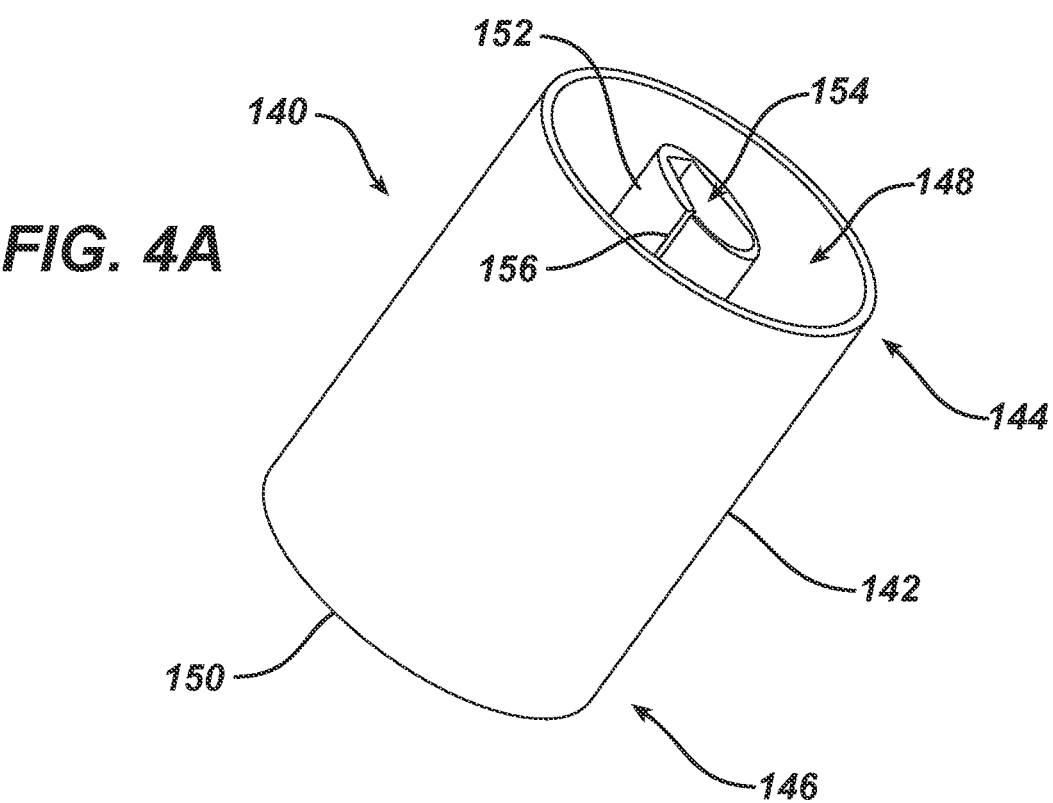
FIG. 4A shows a perspective view of a proximal end of a suture needle container having a mandrel used for aligning a needle driver with a tip of a suture needle, in accordance with one embodiment of the present patent application.
Figure 4B:
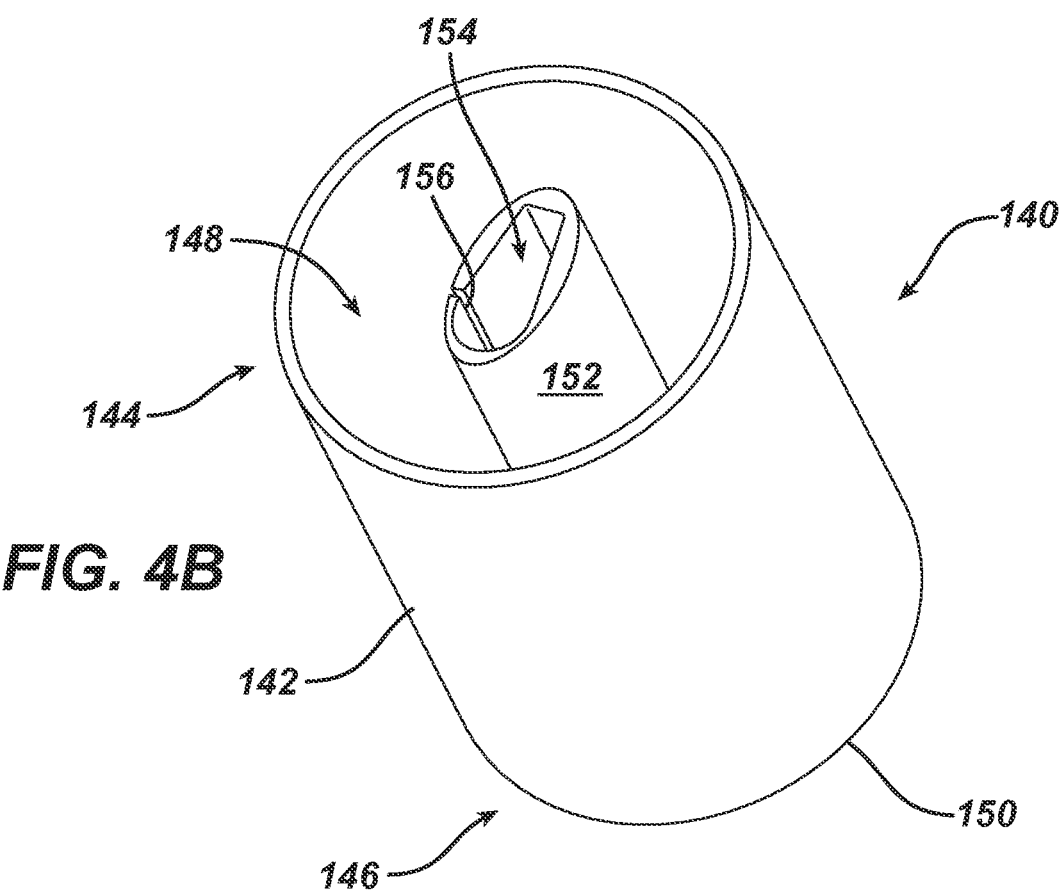
FIG. 4B shows another perspective view of the proximal end of the suture needle container shown in FIG. 4A.

Referring to FIGS. 4A and 4B, in one embodiment, a suture needle container 140 contains a suture needle, such as the suture needle 100 shown and described above in FIGS. 1A-1B. In one embodiment, a needle driver, such as the needle driver 116 shown and described above in FIGS. 3A-3D, may be utilized to remove the suture needle from the suture needle container. In one embodiment, the suture needle container 140 preferably includes an outer wall 142 having a proximal end 144 that is open and a distal end 146 that is closed. In one embodiment, the outer wall 142 has a cylindrical shape. In one embodiment, the suture needle container 140 preferably includes an opening 148 provided at the proximal end 144 of the outer wall 142 that enables a needle driver to pass through the opening to access a suture needle stored in the suture needle container. In one embodiment, the suture needle container 140 preferably includes an end wall 150 that closes the distal end 146 of the outer wall 142. The end wall 150 preferably defines the closed end of the suture needle container 140.

In one embodiment, the suture needle container 140 preferably includes a mandrel 152 that is located inside the outer wall 142. The mandrel 152 may be centrally located inside the perimeter of the outer wall 142. In one embodiment, the mandrel 152 preferably extends from the opening 148 at the proximal end 144 of the outer wall 142 to the end wall 150 at the distal end 146 of the outer wall 142. In one embodiment, the mandrel 152 preferably has a needle driver guide channel 154 that is adapted to receive a distal end of the needle driver and guide distal movement of the needle driver toward the end wall 150 of the suture needle container 140. The mandrel 152 desirably has a suture needle slot 156 that is adapted to hold a suture needle, such as an elastic suture needle, for being loaded onto a distal end of a needle driver when the distal end of the needle driver is inserted into the needle driver guide channel 154.

Figure 4C:
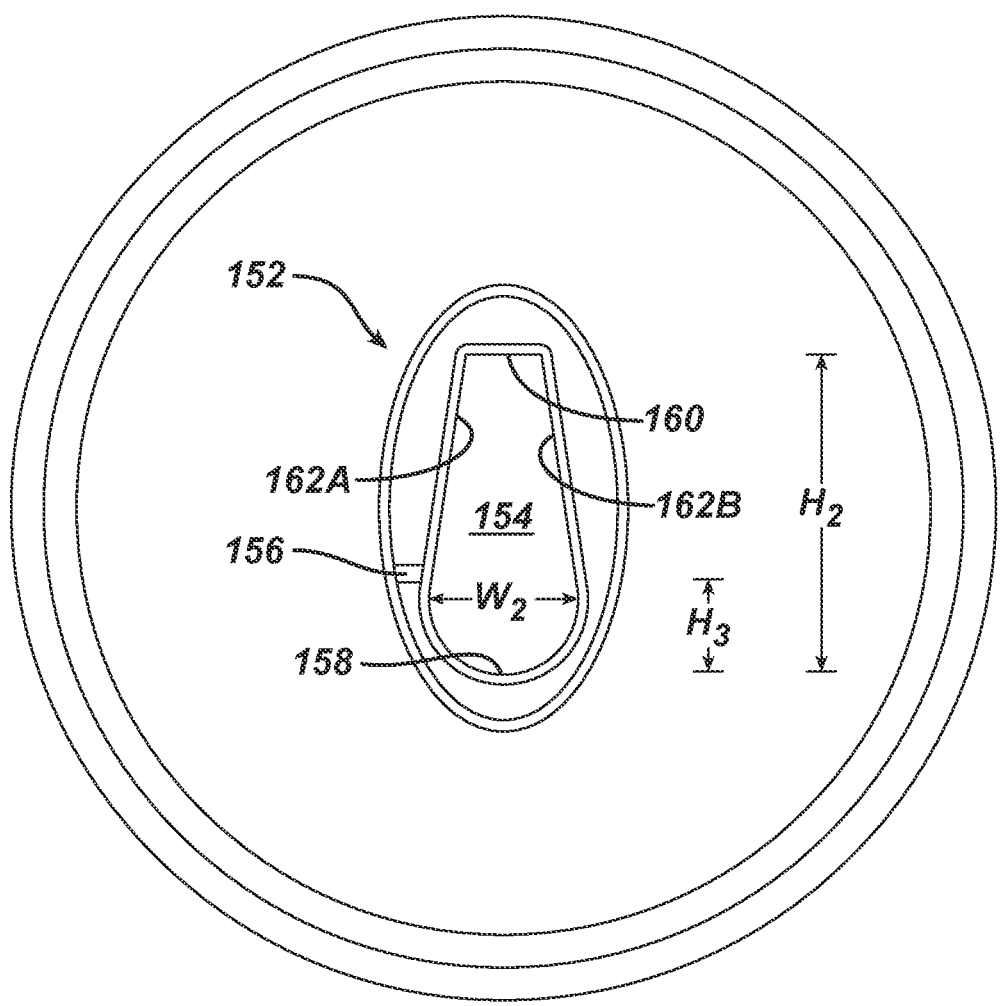
FIG. 4O shows a proximal end view of the suture needle container shown in FIGS. 4A and 4B.
FIG. 4D shows another perspective view of the proximal end of the suture needle container shown in FIGS. 4A-4O.
FIG. 4E shows another perspective view of the proximal end of the suture needle container shown in FIGS. 4A-4D.

Referring to FIG. 4C, in one embodiment, the mandrel 152 preferably includes a floor 158 that defines a lower end of the needle driver guide channel 154. In one embodiment, the floor 158 may have a concave surface that closely matches the shape of the outer surface of the elongated shaft of the needle driver. In one embodiment, when the needle driver is inserted into the needle driver guide channel 154, an underside of the elongated shaft of the needle driver may engage and slide over the concave shaped floor 158. In one embodiment, the mandrel 152 preferably includes a ceiling 160 that defines an upper end of the needle driver guide channel 154. In one embodiment, the ceiling 160 may has a flat surface that opposes the concave floor 158. In one embodiment, the mandrel 152 may include first and second lateral side walls 162A, 162B that extend between the floor 158 and the ceiling 160 for defining the sides of the needle driver guide channel 154.

In one embodiment, the needle driver guide channel 154 preferably has a height $H_2$ that extends from the floor 158 to the ceiling 160, and a width $W_2$, measured at a location that is between the suture needle slot 156 and the floor 158, which extends between the first and second lateral side walls 162A, 162B. In one embodiment, the height $H_2$ of the needle driver guide channel 154 preferably matches the height $H_1$ of the clamping assembly 124 when the lower and upper jaws 126, 128 of the clamping assembly are in the open position (FIG. 2B). In one embodiment, the width $W_2$ of the needle driver guide channel 154 (i.e., at a location between the suture needle slot and the concave floor) preferably matches the outer diameter or width $W_1$ of the elongated shaft 118 of the needle driver 116 (FIG. 3A) to guide and control distal movement of the needle driver through the needle driver guide channel 154.

In one embodiment, the suture needle slot 156 provided in the mandrel 152 is spaced above the concave floor 158 of the mandrel 152 by a distance $H_3$ that is greater than ½ of the outer diameter or width $W_1$ of the elongated shaft 118 of the needle driver 116, which insures that the top surface of the lower jaw is positioned between the suture needle slot 156 and the floor 158 of the mandrel 152 when the distal end of the needle driver is inserted into the needle driver guide channel.

As a result, when the damping assembly at the distal end of the needle driver is inserted into the needle driver guide channel 154 of the mandrel 152, the lower jaw of the needle driver is located below the suture needle slot 156 so that the top surface of the lower jaw is positioned below the tip of the suture needle, and the upper jaw of the needle driver is located above the suture needle slot 156 so that the bottom surface of the upper jaw is positioned above the tip of the suture needle.

Figure 4D:
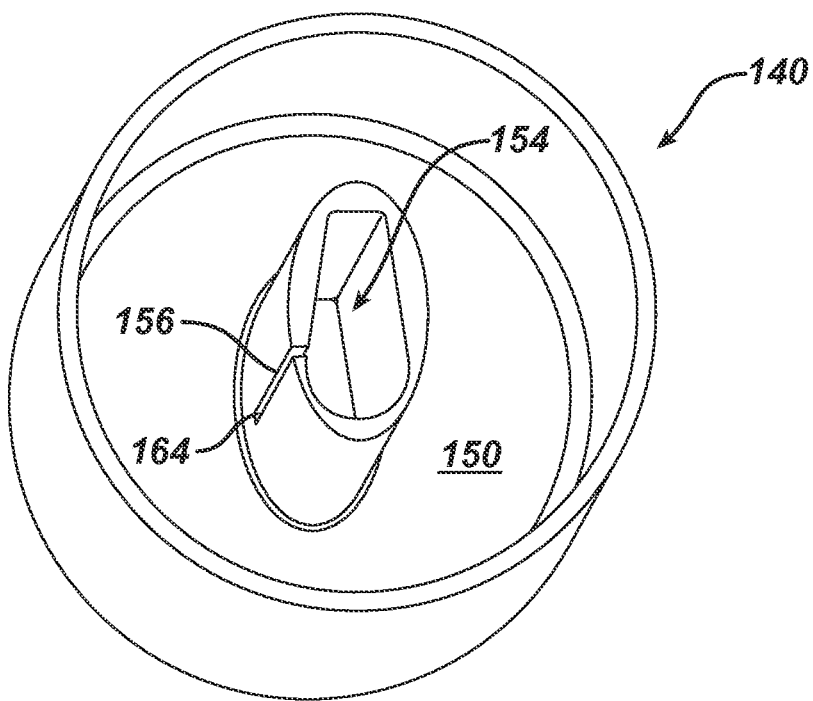
Figure 4E:
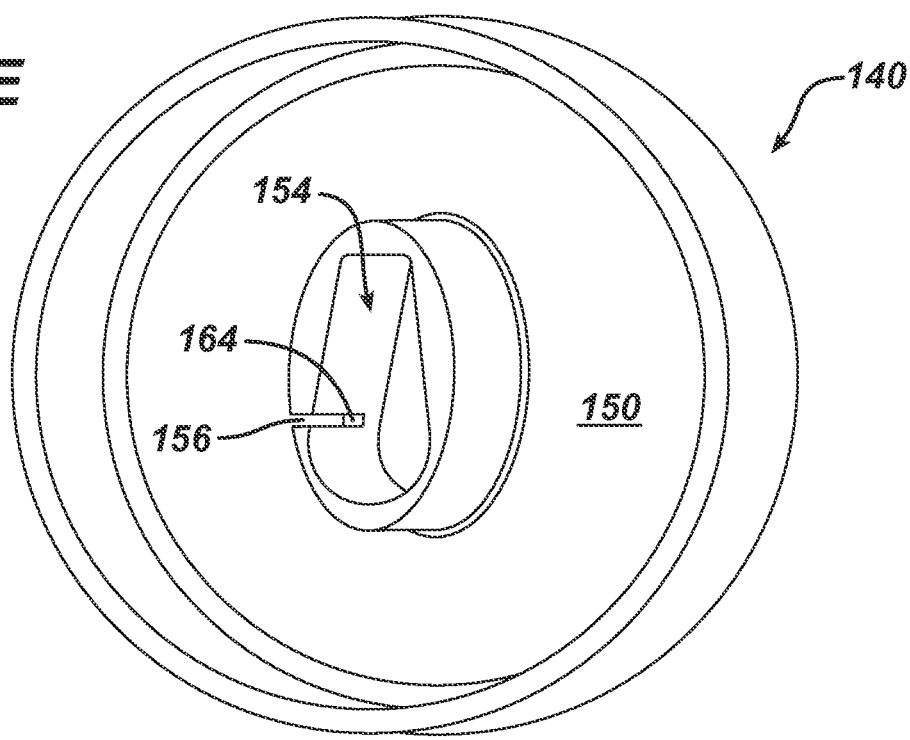

Referring to FIGS. 4D and 4E, in one embodiment, the suture needle slot 156 of the suture needle container 140 preferably has a distal end 164 that is spaced from the end wall 150 at the closed distal end of the suture needle container 140. When positioning a suture needle in the suture needle slot 156, the distal end 164 of the suture needle slot 156 preferably functions as a hard stop so that the suture needle is spaced away from the end wall 150 of the suture needle container 140. Then inserting the needle driver into the needle driver guide channel 154 for loading a suture needle onto the needle driver, the spacing of the distal end 164 of the suture needle slot 156 away from the end wall 150 of the suture needle container 140 desirably enables consistent, reliable and repeatable alignment of the top and bottom surfaces of the respective lower and upper jaws of the clamping assembly with the tip of the suture needle being held within the suture needle slot 156 of the suture needle container 140.

Figure 5A:
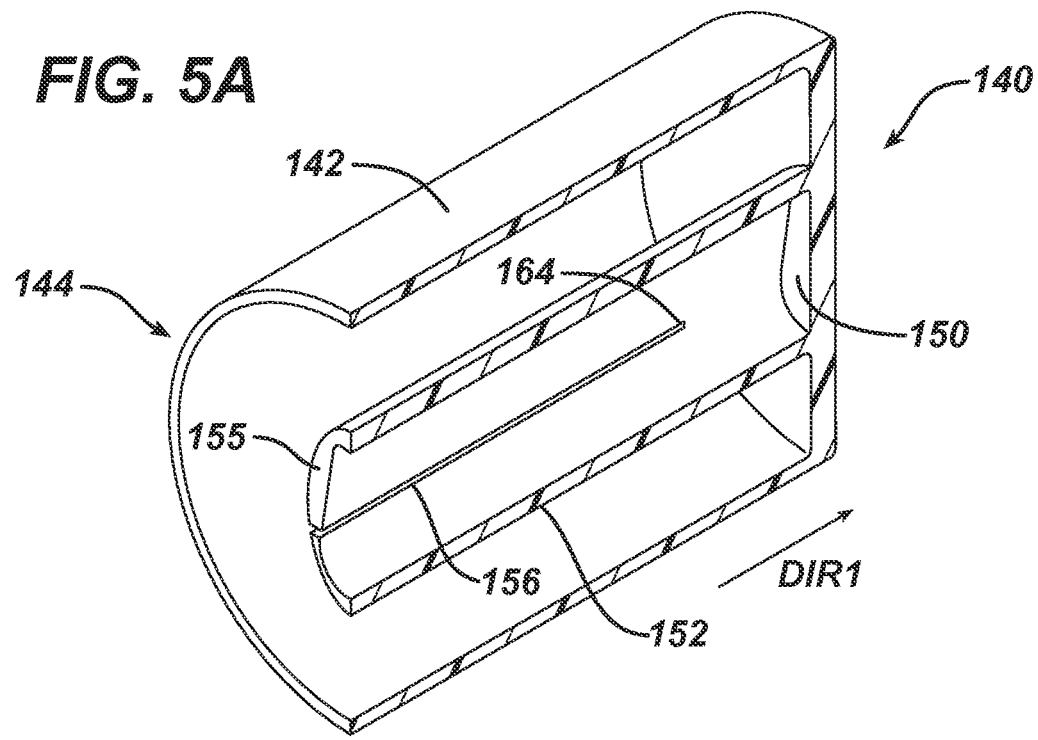
FIG. 5A shows a perspective view of a cross-section of the suture needle container shown in FIGS. 4A-4E.
Figure 5B:
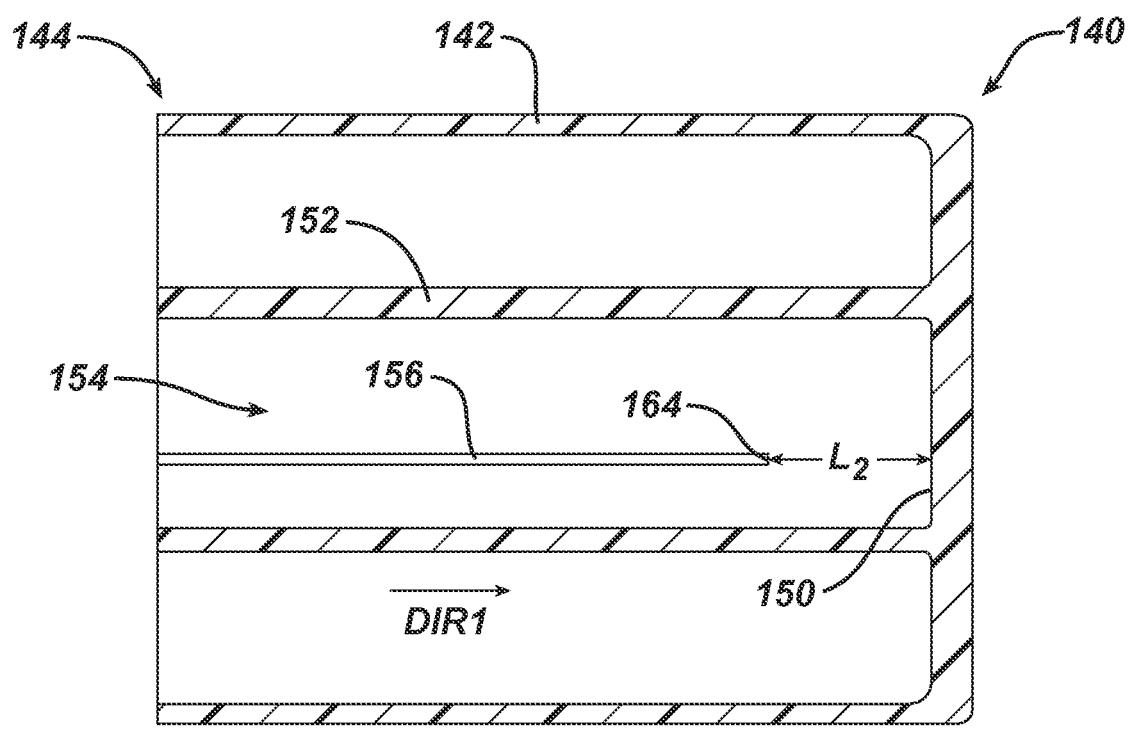
FIG. 5B shows side view of a cross-section of the suture needle container shown in FIGS. 4A-4E and 5A.

Referring to FIGS. 5A and 5B, in one embodiment, the mandrel 152 desirably has a proximal end 155 that is aligned with the proximal end 144 of the outer wall 142 of the suture needle container 140. The suture needle slot 156 is preferably open at the proximal end 155 of the mandrel 152. The suture needle slot 160 has the closed distal end 164 (functioning as a hard stop) that is spaced away from the end wall 150 by a distance $L_2$ that is less than the length $L_1$ of the top surface 130 of the lower jaw 126 (FIG. 3B). In one embodiment, a suture needle may be pre-positioned within the suture needle slot 156 by inserting the suture needle into the open end of the suture needle slot and advancing the suture needle distally through the suture needle slot 156 until the body of the suture needle abuts against the distal end 164 of the suture needle slot 156.

In one embodiment, when the clamping assembly at the distant end of the needle driver is inserted into the open end of the needle driver guide channel 154, the needle driver may be advanced in the direction DIR1 until the distal ends of the lower and upper jaws abut against the end wall 150 of the suture needle container 140. In one embodiment, at that stage of distal advancement, the leading end of the lower jaw will abut against the end wall 150 whereupon the tip of the suture needle will be aligned with the opposing top and bottom surfaces of the respective lower and upper clamping jaws.

Figure 6A:
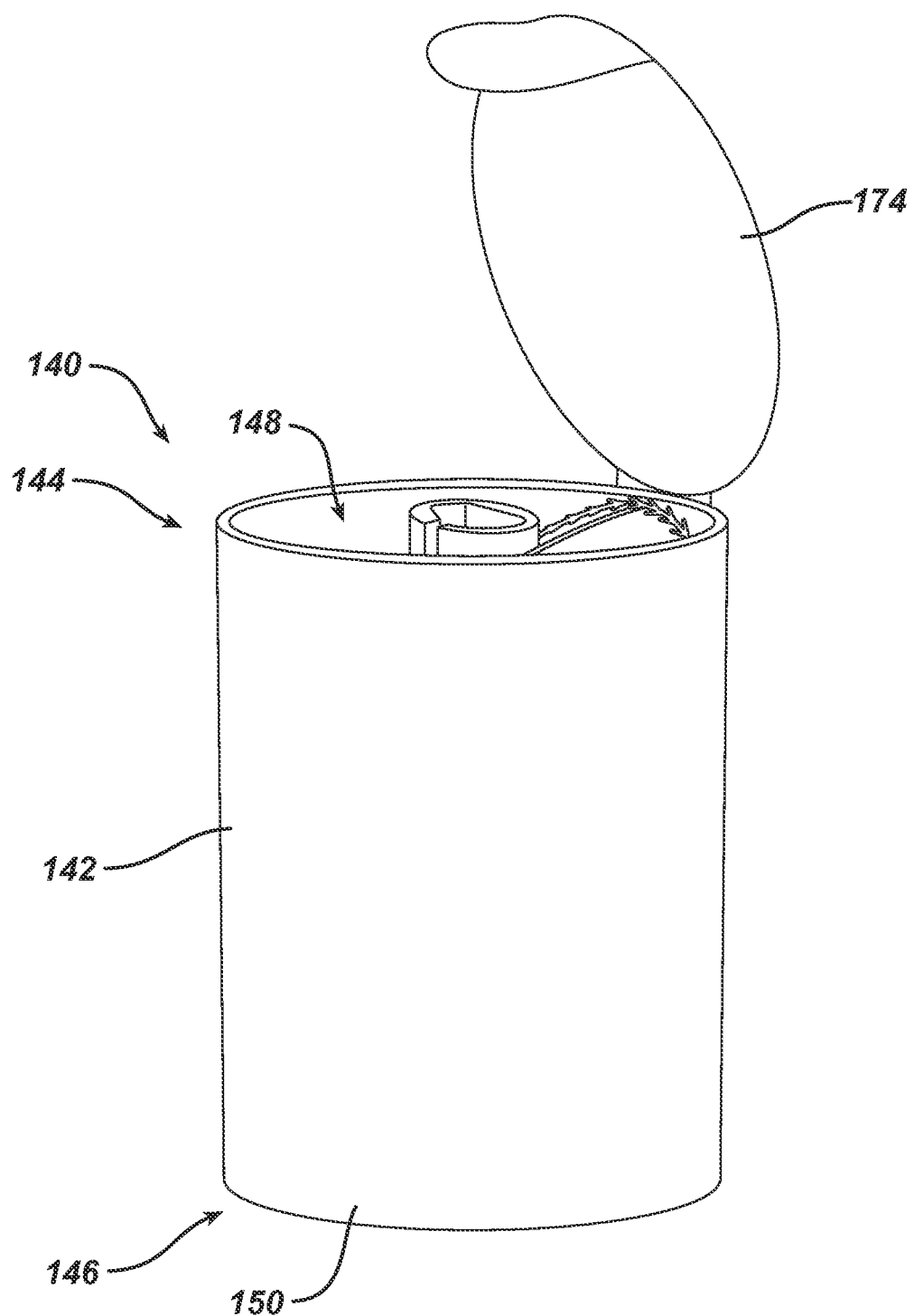
FIG. 6A shows a perspective view of a suture needle container having a cover and loaded with a suture needle and a suture wrapped around a mandrel, in accordance with one embodiment of the present patent application.
Figure 6B:
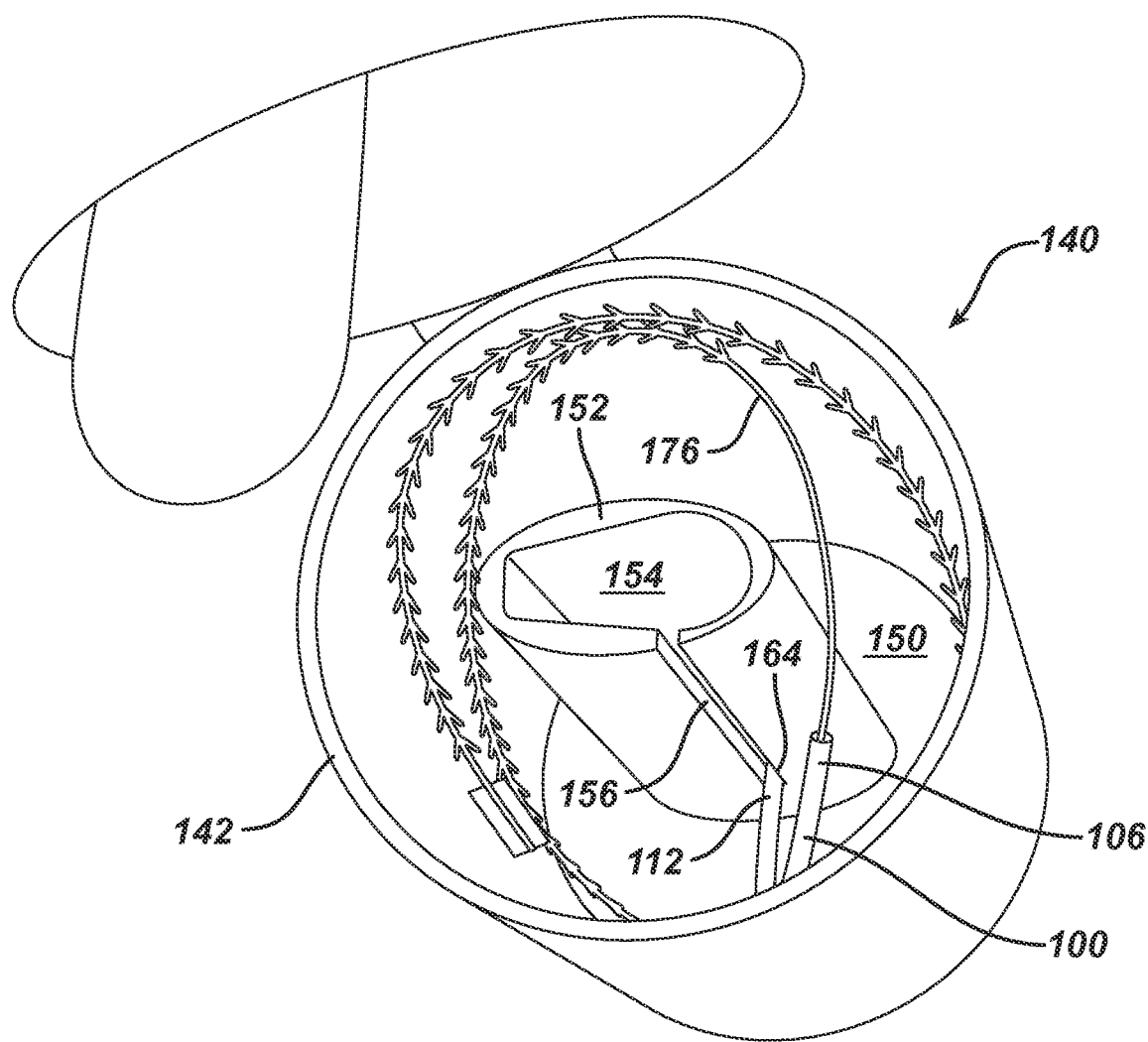
FIG. 6B shows a top perspective view of the suture needle container shown in FIG. 6A.

Referring to FIGS. 6A and 6B, in one embodiment, the suture needle container 140 preferably has the outer wall 142 that extends from the proximal end 144 to the distal end 146. The suture needle container 140 preferably has an opening 148 at the proximal end 144 of the outer wall 142 and the end wall 150 that forms a closed distal end of the suture needle container 140. In one embodiment, the open end 148 of the suture needle container 140 is preferably covered with a cover 174 that may be sealed over the open end 148 of the suture needle container 140. The cover 174 may maintain a sterile environment inside the suture needle container 140 so that the suture needle and the suture remain sterilized during shipment and storage of the suture needle container. In one embodiment, the cover 174 may be made of foil, polymer materials, breathable materials such as high-density polyethylenes (e.g., Tyvek), and any other well-known materials that may be used to maintain sterile environments for medical devices and tools.

Referring to FIG. 6B, in one embodiment, in order to position the suture needle inside the suture needle container, the tip 114 (FIG. 1A) at the distal-most end of the tapered section 112 of the suture needle 100 is preferably inserted into the suture needle slot 156 of the mandrel 152 so that the tip is located inside the needle driver guide channel 154 and a trailing section of the suture needle is located between the mandrel 152 and the outer wall 142 of the suture needle container 140. The tip of the suture needle 100 may be advanced toward the end wall 150 of the suture needle container 140 until the tapered section 112 of the suture needle abuts against the terminal end 164 (FIG. 5B) of the suture needle slot 156. In one embodiment, the suture needle 100 preferably has a surgical suture 176 attached to a suture attachment opening at the proximal end 106 of the suture needle 100. The suture 176 may be wrapped around the mandrel 152 for being stored inside the suture needle container 140, between the outer surface of the mandrel and the inner surface of the outer wall 142.

Figure 7:
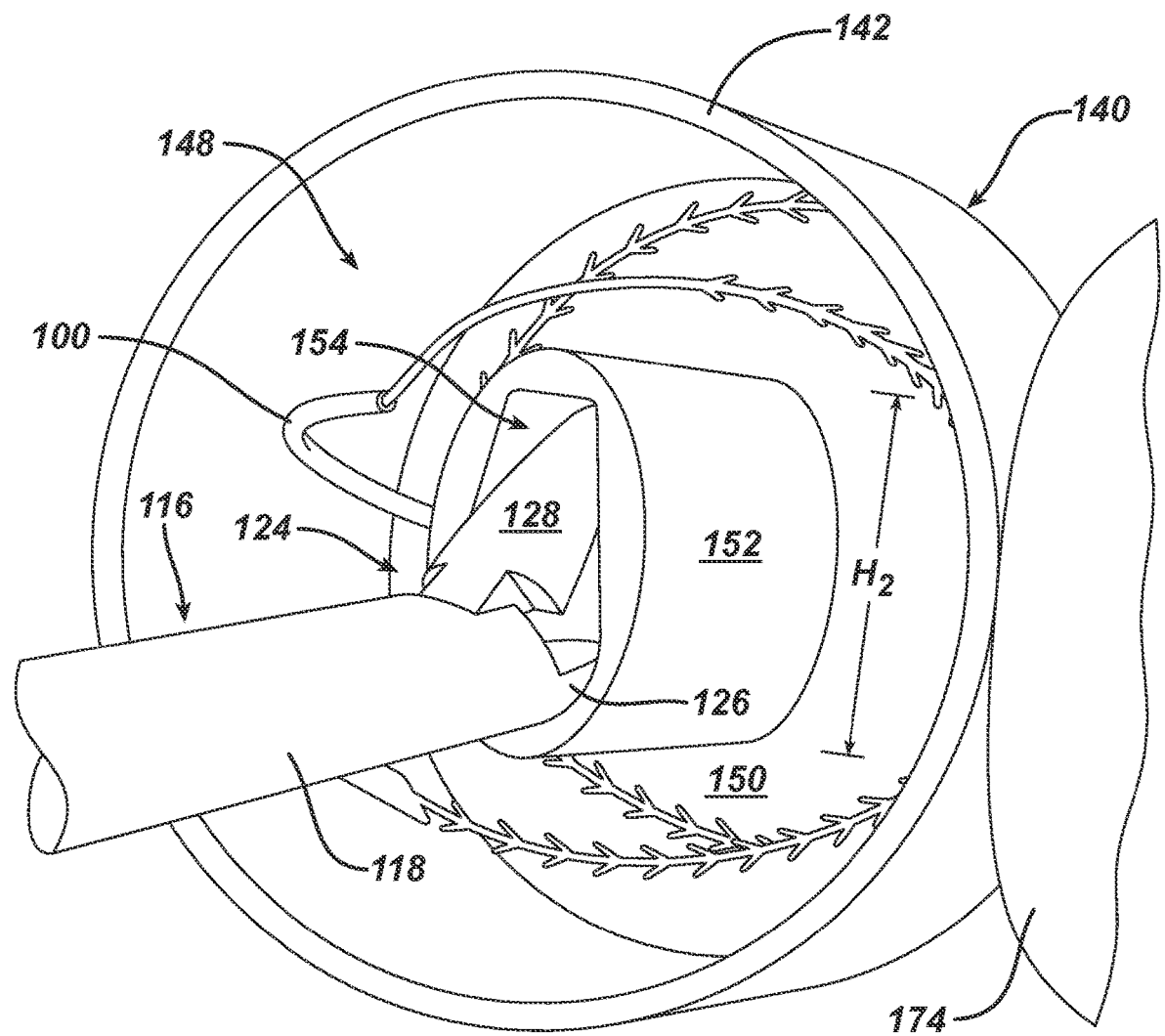
FIG. 7 shows a first step of a method of removing a suture needle from a suture needle container, in accordance with one embodiment of the present patent application.

Referring to FIG. 7, in one embodiment, in order to remove the suture needle 100 from the suture needle container 140, the cover 174 is preferably removed (e.g., pierced, peeled away, cut, etc.) to access the opening 148 at the proximal end of the outer wall 142 of the suture needle container 140. Once the cover 174 has been removed or opened, a distal end of the needle driver 116 may be inserted into the needle driver guide channel 154 of the mandrel 154 with the lower jaw 126 of the damping assembly 124 positioned adjacent the concave floor 158 (FIG. 4C) at the lower end of the needle driver guide channel 154 and the upper jaw 128 (in the open position) extending to the ceiling 160 located at the upper end of the needle driver guide channel. In one embodiment, when the clamping assembly 126 is in the open position, the lower and upper jaws define a height $H_1$ (FIG. 2B) that approximates the height $H_2$ of the needle driver guide channel 154 for guiding and controlling the orientation of the needle driver 116 as the clamping assembly 124 is advanced toward the end wall 150 at the distal end of the outer wall 142 of the suture needle container 140.

Figure 8:
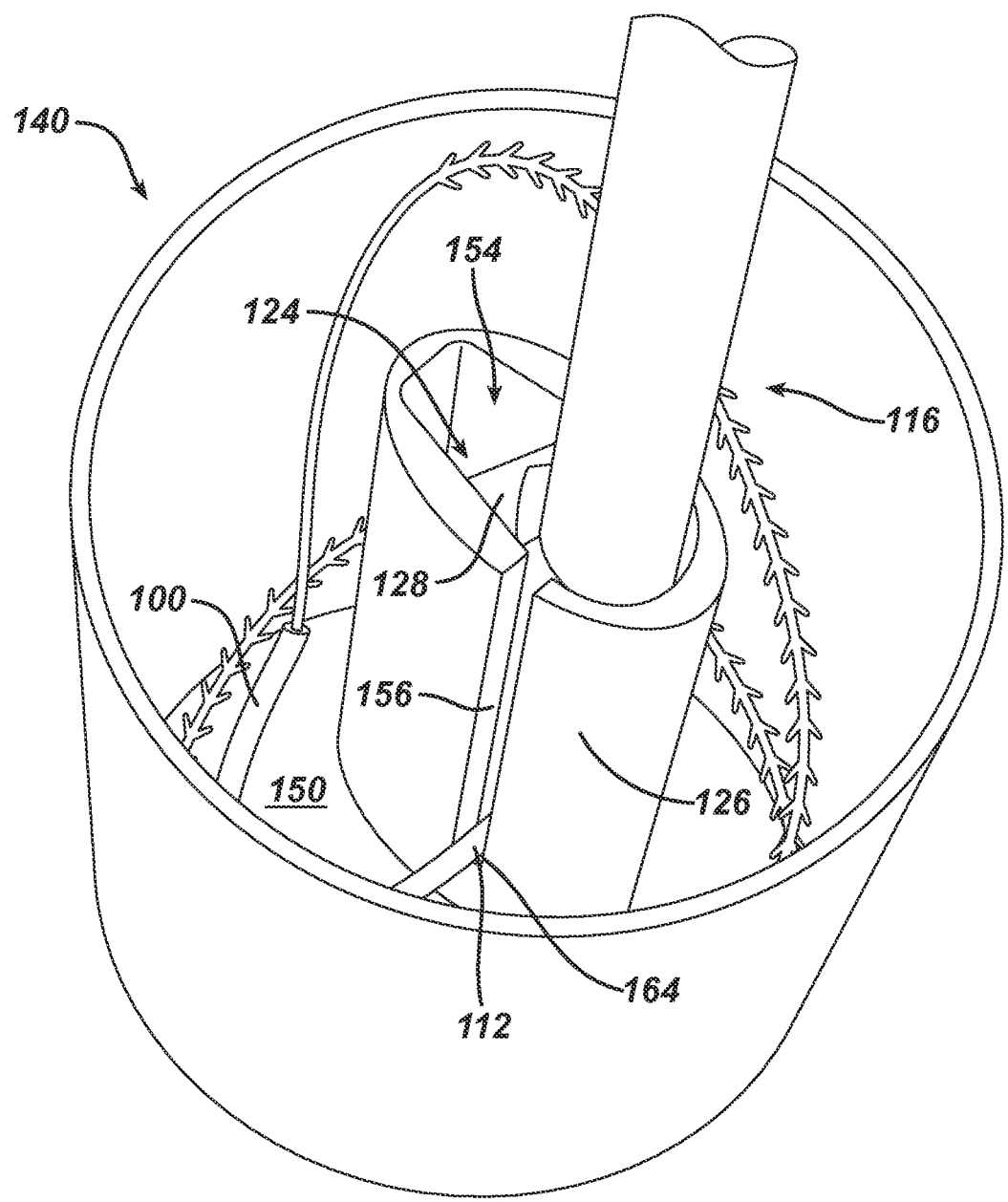
FIG. 8 shows a second step of a method of removing a suture needle from a suture needle container, in accordance with one embodiment of the present patent application.

Referring to FIG. 8, in one embodiment, the tapered section 112 of the suture needle 100 is located at the terminal end 164 of the suture needle slot 156. In one embodiment, the clamping assembly 124 at the distal end of the needle driver 116 is advanced through the needle driver guide channel 154 and toward the end wall 150 of the suture needle container 140 until the distal end of the lower jaw engages the end wall 150. In this position, the opposing top and bottom surfaces of the respective lower and upper jaws 126, 128 of the clamping assembly 124 are preferably aligned with the tip of the suture needle 100, which is located inside the needle driver guide channel 154.

Figure 9:
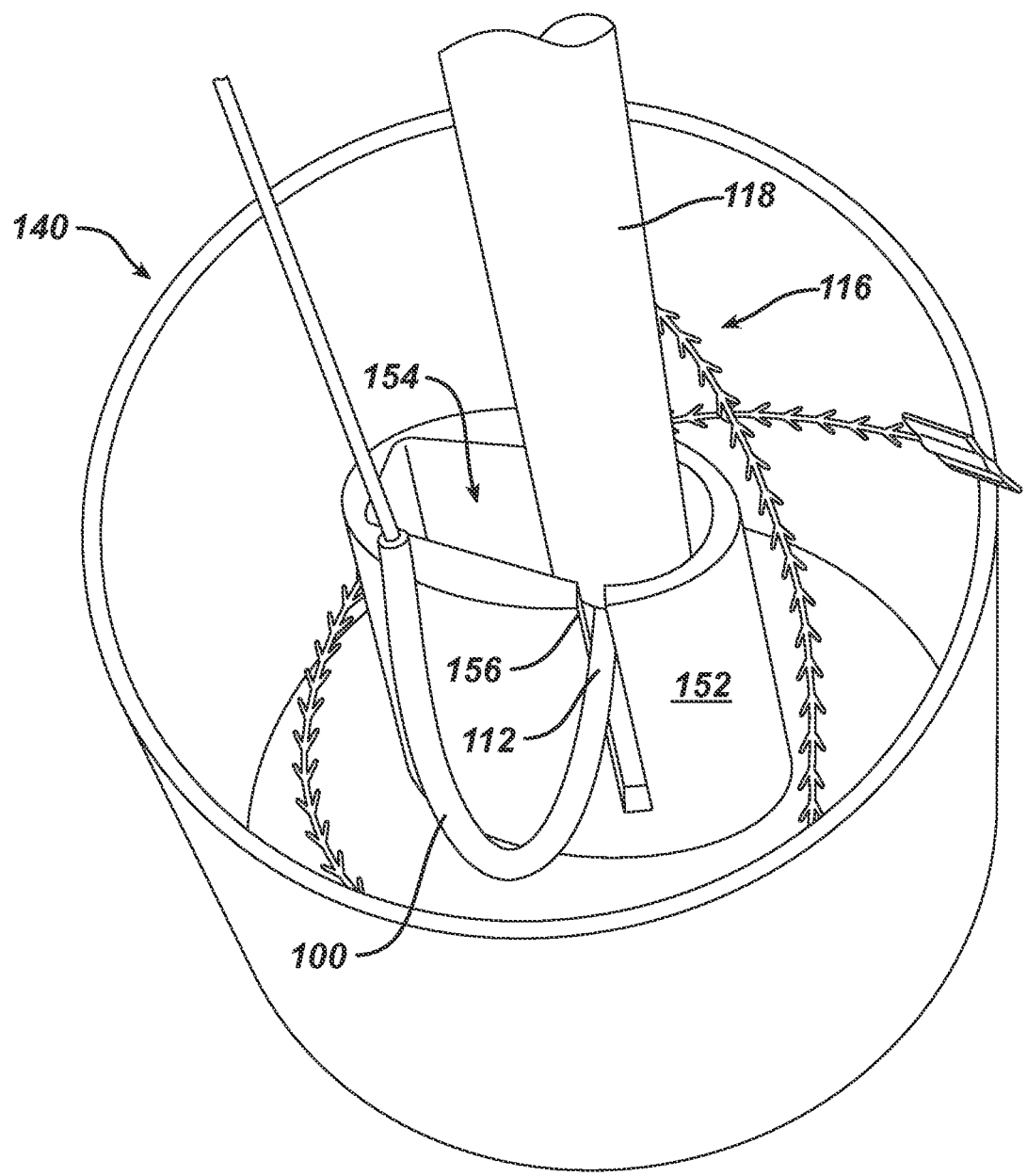
FIG. 9 shows a third step of a method of removing a suture needle from a suture needle container, in accordance with one embodiment of the present patent application.

Referring to FIG. 9, in one embodiment, after the opposing faces of the respective lower and upper clamping jaws have been aligned with the distal tip of the suture needle 100, the clamping assembly is preferably moved to the closed position so that the opposing faces of the lower and upper clamping jaws engage the tapered section of the suture needle 100 that is proximal to the distal tip of the suture needle. With the clamping assembly in the closed position for securing the suture needle 100, the elongated shaft 118 of the needle driver 116 may be retracted from the needle driver guide channel 154 for removing the suture needle 100 from the proximal, open end of the suture needle slot 156 of the mandrel 152. In one embodiment, as the suture needle 100 is extracted from the suture needle container 140, the tapered section 112 of the suture needle 100 slides through the suture needle slot 156 toward the proximal, open end of the suture needle slot.

Figure 10:
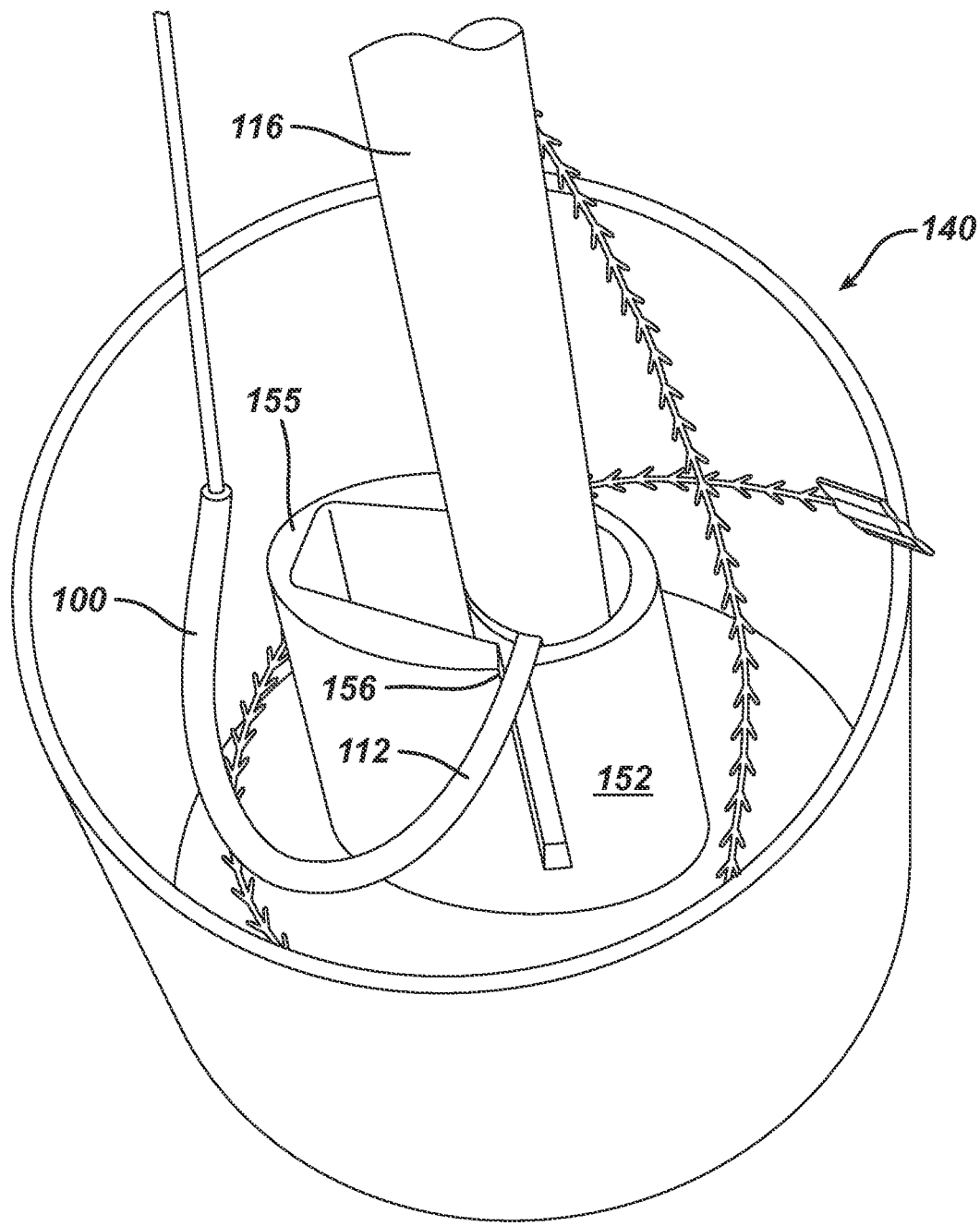
FIG. 10 shows a fourth step of a method of removing a suture needle from a suture needle container, in accordance with one embodiment of the present patent application.

FIG. 10 shows the suture needle 100 during further extraction from the suture needle container 140. The tapered section 112 of the suture needle 100 is secured by the clamping assembly 124 of the needle driver 116. The tapered section 112 is removed from the open end of the suture needle slot 156 at the proximal end 155 of the mandrel 152.

FIGS. 11A-11B, 12A-12B, and 13A-13B show a system and method of using a needle driver for removing a suture needle from a suture needle container, in accordance with one embodiment of the present patent application. The system and method may incorporate robotics so that the steps are performed using computer software, hardware, processors and robotics technology.

Referring to FIGS. 11A and 11B, in one embodiment, the mandrel 152 of the suture needle container 140 preferably includes a floor 158, a ceiling 160, and first and second lateral guide walls 162A, 162B that define a needle driver guide channel 152 that extends from a proximal end 155 of the mandrel to the distal end wall 150 of the needle driver container. The mandrel 152 includes a suture needle slot 156 adapted to hold a suture needle that has an open end at the proximal end 155 of the mandrel 152 and a terminal end 164 that is spaced proximally from the end wall 150 by the distance $L_2$. The suture needle slot 156 holds the tip 114 and part of the tapered section 112 of the suture needle inside the needle driver guide channel 154 of the mandrel 152 so that lower and upper jaws of a clamping assembly of a needle driver may be advanced into alignment with the tip 114 and the part of the tapered section.

Referring to FIGS. 12A and 12B, in one embodiment, the clamping assembly 124 of the needle driver 116 is inserted into the proximal end 155 of the mandrel 152 with the lower jaw 126 and the upper jaw 128 (FIG. 12A) in the open position. The lower jaw 126 is positioned over the floor 158 of the mandrel 152 and the upper jaw 128 is positioned adjacent the ceiling 160 of the mandrel. The lower and upper jaws 126, 128 define a height $H_1$ that matches the height $H_2$ of the needle driver guide channel 154 that extends from the floor 158 to the ceiling 160. The elongated shaft 118 of the needle driver 116 has a width $W_1$ that matches the width $W_2$ of the needle driver guide channel 154. Thus, the needle driver guide channel 154 preferably has a shape and configuration that closely conforms to the shape of the distal end of the needle driver 116 for controlling the orientation and advancement of the needle driver 116 as is moves through the needle driver guide channel 154 in the distal direction DIR1.

In one embodiment, the mandrel 152 preferably includes the suture needle slot 156 having a lower end that is spaced a distance $H_3$ above the floor 158 of the mandrel 152. In one embodiment, the distance $H_3$ is greater than ½ the outer diameter of the elongated shaft 118 of the needle driver 116. As a result, when the lower jaw 126 is inserted into the needle driver guide channel 154 for sliding over the floor 158 of the needle driver guide channel 154, the top surface 130 of the lower jaw 126 will be located between the suture needle slot 156 and the floor 158 of the mandrel, thereby insuring that the top surface 130 of the lower jaw 126 will be positioned under the tip 114 of the suture needle 100.

Referring to FIGS. 13A and 13B, in one embodiment, the needle driver 116 is advanced distally in the needle driver guide channel 154 until the distal end 175 of the lower jaw 126 abuts against the end wall 150 of the suture needle container. The terminal end 164 of the suture needle slot 156 holds the tip 114 of the suture needle 100 at a distance $L_2$ from the end wall 150. The top surface 130 of the lower jaw 126 has a length $L_1$ that is greater than the distance $L_2$ between the tip 114 of the suture needle and the end wall 150. As such, when the distal end 175 of the lower jaw 126 abuts against the end wall 150 of the suture needle container, the top surface 130 of the lower jaw 126 is aligned with the tip 114. In one embodiment, the tip is preferably positioned about midway along the length of the top surface of the lower jaw. In addition, the bottom surface 132 of the upper jaw 128, which mirrors the top surface 130 of the lower jaw 126, is also aligned with the tip 114. Due to the suture needle slot 156 being positioned above the top surface 130 of the lower jaw 126, the tip 114 of the suture needle is desirably positioned between the clamping faces of the lower and upper jaws 126, 128.

When the clamping assembly 124 of the needle driver 116 is moved to the closed position to secure the suture needle 100 between the lower and upper jaws 126, 128, the top and bottom faces 130, 132 of the respective lower and upper jaws preferably engaged the tapered section 112 of the suture needle 100 that is located between the jaws. In one embodiment, the lower and upper jaws 126, 128 preferably clamp onto the tapered section 112 of the suture needle 100 and are spaced away from the tip 114 of the suture needle because engaging the tip with the top and bottom clamping surfaces may damage, mar, dull, bend and/or deform the tip of the suture needle so that the tip is unfit for its intended purpose (e.g., a suturing operation). In one embodiment, when the clamping assembly 124 is in the closed position for securing the suture needle, the top and bottom clamping surfaces 130, 132 of the respective lower and upper jaws 126, 128 preferably completely surround the tip 114 of the suture needle 100 so that the tip is protected by the jaws as the needle driver 116 pushes or pulls the loaded suture needle through a trocar.

Figure 14A:
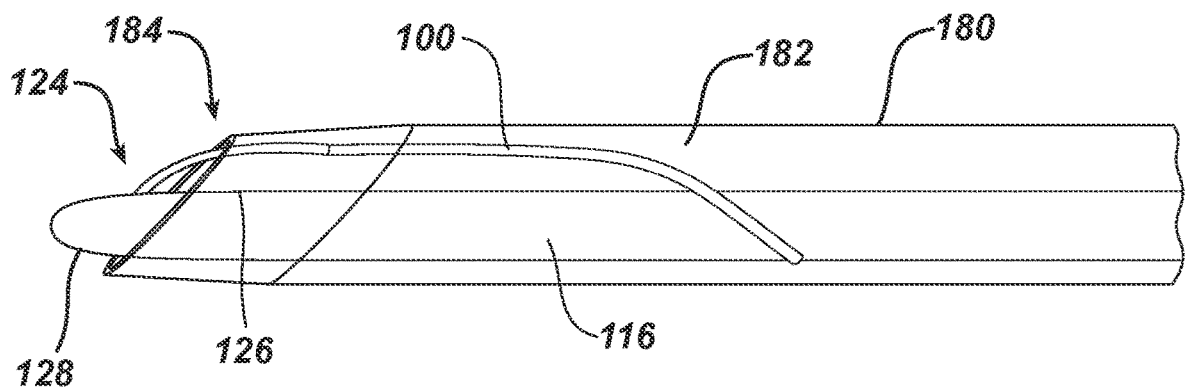
FIG. 14A shows a stage of a method of using a needle driver to advance an elastic suture needle toward a distal end of a trocar, in accordance with one embodiment of the present patent application.

Referring to FIG. 14A, in one embodiment, after an elastic, hyper-elastic or superelastic suture needle 100 has been loaded onto the needle driver 116, the needle driver 116 may be utilized for advancing the suture needle 100 through a trocar 180 for positioning the suture needle at a surgical site. In one embodiment, the trocar 180 preferably has an elongated conduit 182 defining an inner diameter that extends to an opening at a distal end 184 of the trocar. The clamping assembly 124 of the needle driver 116 is preferably advanced through the conduit 182 of the trocar 180 for pulling the suture needle 100 through the trocar. As the suture needle 100 is pulled by the clamping assembly 124 toward the distal end 184 of the trocar 180, the elongated body 102 of the superelastic suture needle 100 preferably elastically deforms (e.g., straightens out, flattens out, assumes a lower profile).

Figure 14B:
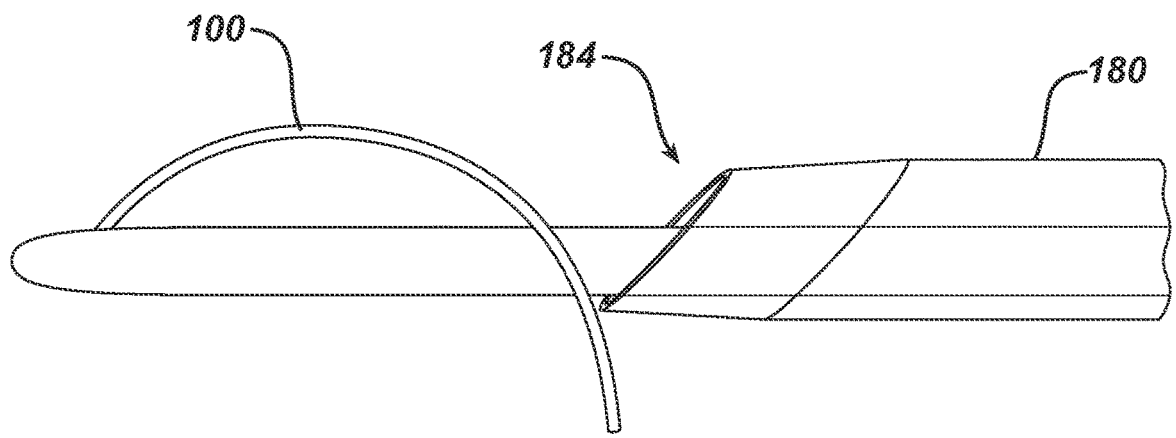
FIG. 14B shows the needle driver and the elastic suture needle of FIG. 14A after the suture needle has been advanced beyond the distal end of the trocar for being located at a surgical site, in accordance with one embodiment of the present patent application.
Figure 14C:
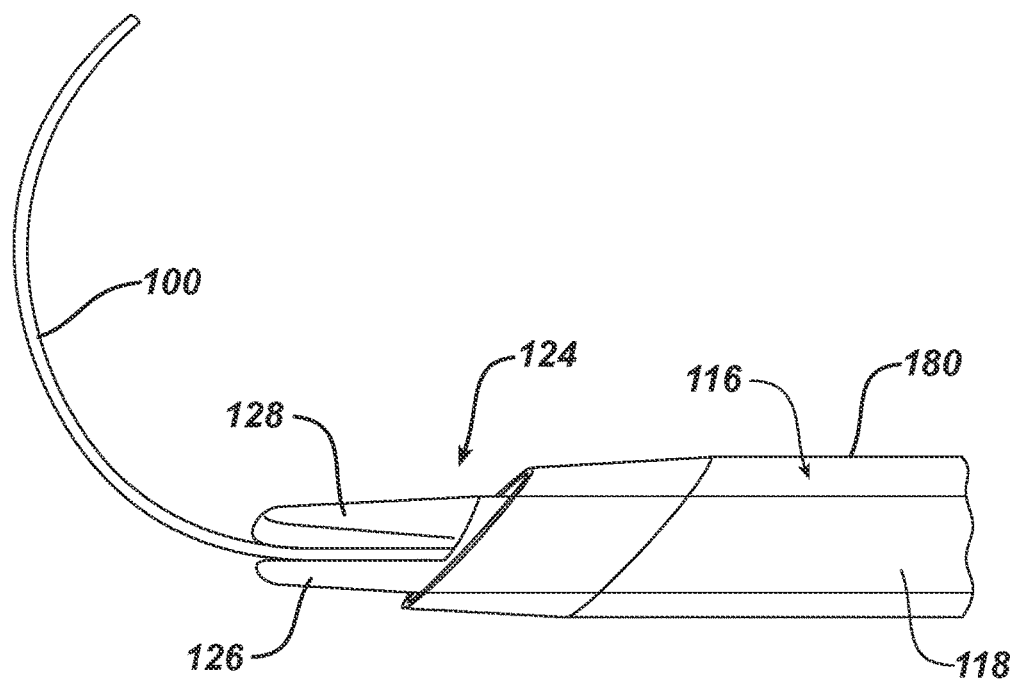
FIG. 14C shows a stage of a method of using a needle driver to retract the elastic suture needle from a surgical site and toward a proximal end of the trocar, in accordance with one embodiment of the present patent application.

Referring to FIG. 14B, after the clamped suture needle 100 has been advanced beyond the distal end 184 of the trocar 180, the suture needle 100, having elastic properties, preferably returns to the original curved configuration (e.g., a half circle shape). Surgical personnel may then utilize the curved suture needle 100 for performing a suturing operation at the surgical site.

Referring to FIG. 14O, in one embodiment, at the conclusion of a suturing operation, the suture needle 100 may be removed from a patient by retracting the suture needle through the trocar 180. In one embodiment, the clamping assembly 124 is again closed for securing the distal end of the curved suture needle 100 between the lower jaw 126 and the upper jaw 128 of the needle driver 116.

Figure 14D:
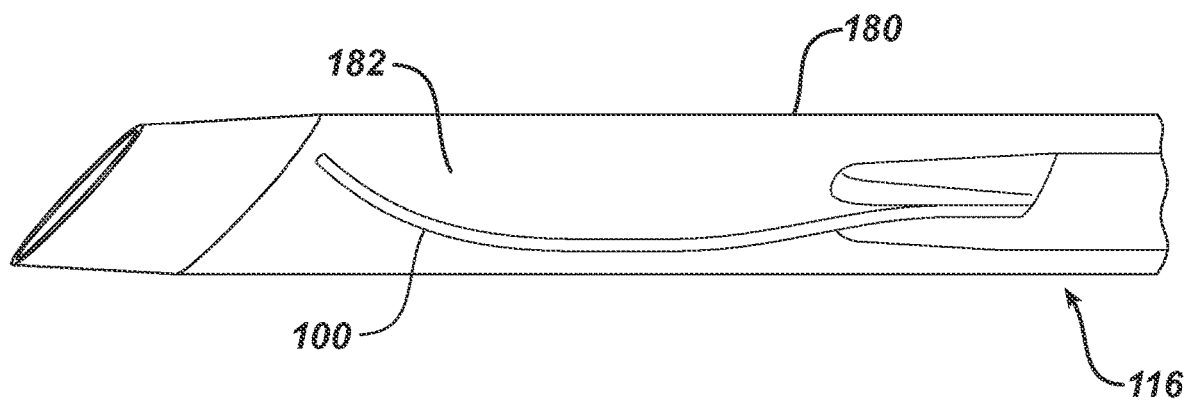
FIG. 14D shows a later stage of a method of retracting the elastic suture needle toward the proximal end of the trocar, in accordance with one embodiment of the present patent application.

Referring to FIG. 14D, in one embodiment, the suture needle 100 may be retracted through the cannula 182 of the trocar 180. The suture needle 100, having elastic properties, preferably straightens out as it is retracted through the trocar by the clamping assembly 124 of the needle driver 116. As the suture needle is withdrawn through the trocar 180, the lower and upper jaws 126, 128 preferably engage the tapered section of the suture needle 100 and protect the tip to prevent the tip from contacting the inside of the trocar.

In one embodiment, an automated or robotic system may be utilized for loading suture needles onto needle drivers. The suture needles may be packaged inside different suture needle containers (e.g., a can shaped receptacle) or packages that maintain the suture needles and attached sutures in a sterile environment prior to use during a surgical procedure. The suture needle containers may be stored on a rack or in a matrix with each container having a unique identification number or code assigned thereto.

Figure 15:
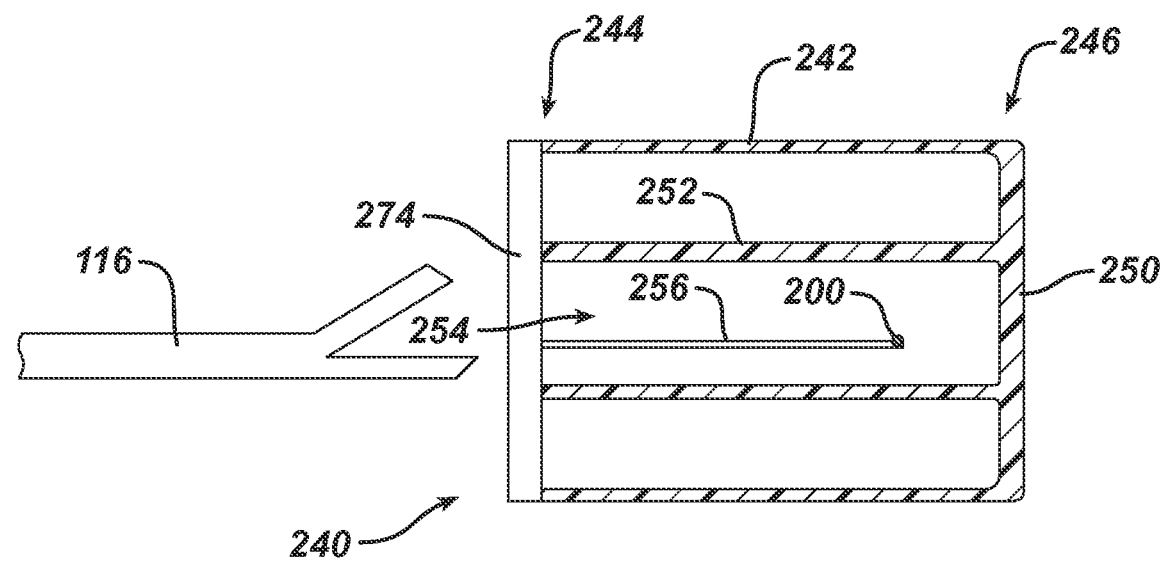
FIG. 15 shows a first step of a method of securing a suture needle to a clamping assembly at a distal end of a needle driver, in accordance with one embodiment of the present patent application.

Referring to FIG. 15, in one embodiment, a suture needle container 240 preferably has an outer wall 242 that extends from a proximal end 244 to a distal end 246 thereof. The proximal end 244 is preferably covered by a cover 274 that maintains a sterile environment for one or more suture needles and one or more sutures stored inside the container. In one embodiment, the cover 274 may be pierced by a distal end of a needle driver 116 for removing a suture needle and suture (not shown) that are pre-loaded inside the suture needle container 240. The suture needle container 240 preferably includes an end wall 250 that forms a closed end of the container. The suture needle container 240 desirably includes a mandrel 252 having a needle driver guide channel 254 and a suture needle slot 256 that may be used for holding a suture needle 200 inside the suture needle container 240.

In one embodiment, the sealed cover 274 provides a sterile environment inside the suture needle container 240. As a result, the suture needle pre-positioned inside the suture needle container 240 may be stored in a sterile environment until the suture needle is required for use during a surgical procedure.

Figure 16:
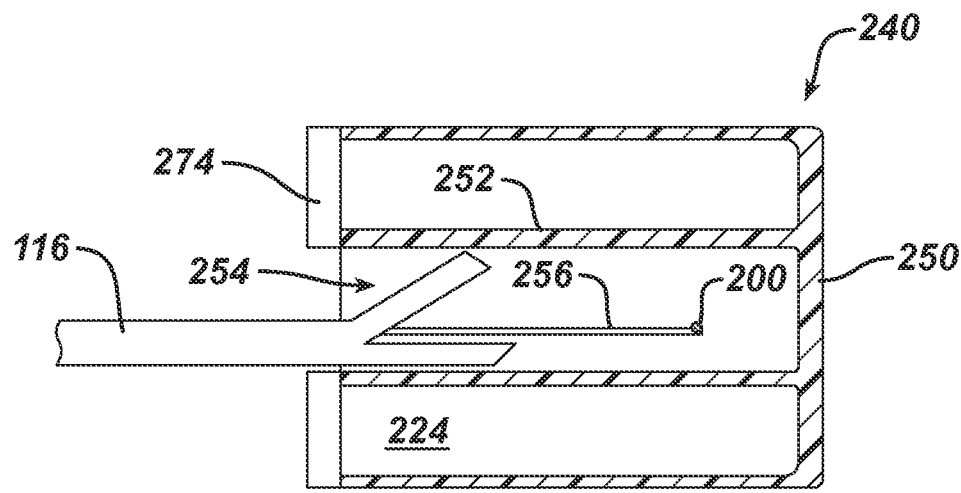
FIG. 16 shows a second step of a method of securing a suture needle to a clamping assembly at a distal end of a needle driver, in accordance with one embodiment of the present patent application.

Referring to FIG. 16, in one embodiment, a distal end of a needle driver 116 may be advanced toward the end wall 250 for piercing the cover 274 to provide access to the suture needle 200 and the suture stored within the suture needle container 240. After the distal end of the needle driver 116 pierces the cover 274, the clamping assembly 224 at the distal end of the needle driver 116 may be advanced into the suture needle guide channel 254 of the mandrel 252 for accessing the suture needle 200 pre-positioned at the closed end of the suture needle slot 256.

Figure 17:
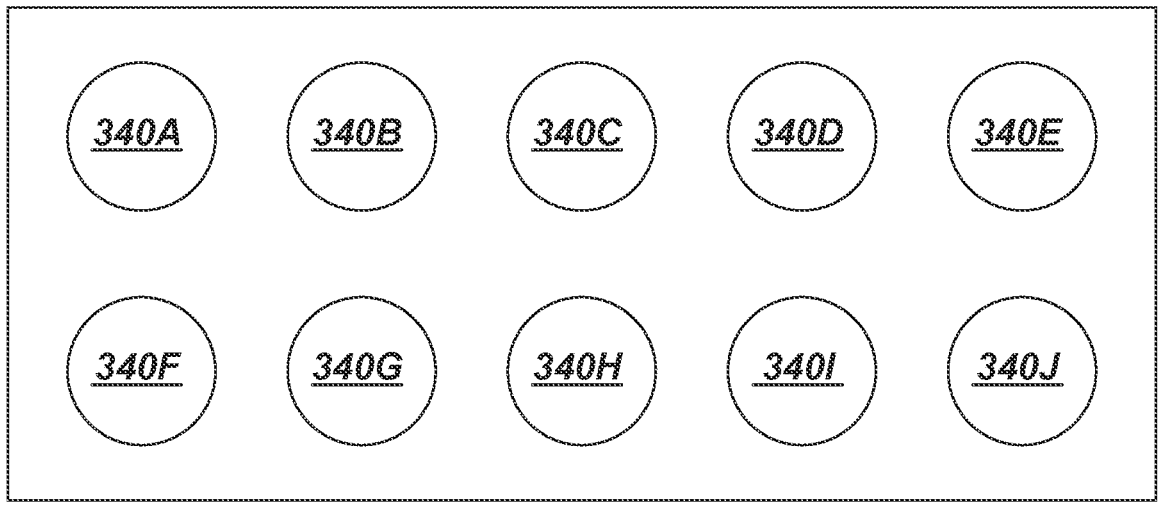
FIG. 17 shows a front view of a rack containing a plurality of suture needle containers, in accordance with one embodiment of the present patent application.

Referring to FIG. 17, in one embodiment, a plurality of suture needle containers 340A-340H, having a structure similar to that disclosed herein, may be pre-stored (e.g., on a rack or surgical table located in the operating room) for use during a surgical procedure. Each of the suture needle containers may contain a different type of suture needle so that a surgeon will have the ability to select to use different types of suture needles during a surgical procedure. For example, a surgeon may want to use a first type of suture needle for suturing delicate tissue and a second type of suture needle for suturing an organ.

In one embodiment, the suture needle containers have a cylindrical shape (i.e., a circular cross-section) with a removable cover overlying an open end of the container. In one embodiment, each of the suture needle containers 340A-340H contains a unique identifier (e.g., a bar code, an electronic chip) that identifies the particular type of suture needle and/or suture needle and suture combination that is disposed inside the container. In one embodiment, a first suture needle container 340A may contain a stainless steel needle and a non-barbed suture attached to a proximal end of the stainless steel suture needle. A second suture needle container 340B may contain a superelastic suture needle having a barbed suture attached to a proximal end thereof. Other combinations of suture needles made of certain materials (e.g., stainless steel, Ethalloy, Nitinol, etc.) and sutures (e.g., barbed, unbarbed, etc.) may be contained within other suture needle containers 340C-340H. Thus, medical personnel have the ability to select from a wide range of different combinations of suture needle and sutures for performing various types of surgical procedures and suturing operations.

Figure 18:
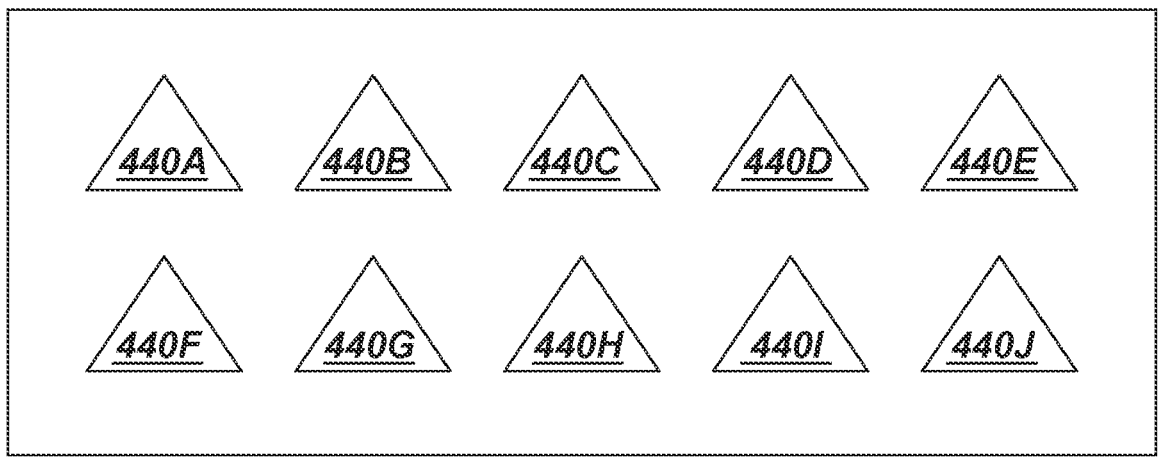
FIG. 18 shows a front view of a rack containing a plurality of suture needle containers, in accordance with one embodiment of the present patent application.

Referring to FIG. 18, in one embodiment, a plurality of suture needle containers 440A-440H may be pre-stored for use during a surgical procedure. In one embodiment, the suture needle containers have a pyramid shape (e.g., a triangle-shaped cross-section) with a sealed cover overlying an open end of the container for maintaining a sterile environment for suture needles and sutures loaded inside the containers. The pyramid shape of the containers may be used to orient the containers to provide an intuitive way for medical personnel to determine the proper orientation of the containers for use with needle drivers. In one embodiment, the suture needle containers may have non-symmetric cross-sections, which enable the containers to be stored or arrayed in only one possible orientation.

In one embodiment, the systems, devices, and methods disclosed herein may be combined with robotic or computer controlled system that enables surgeons to automatically select a particular type of suture needle for use and have the robotic system use computer controlled actuators to access a suture needle container, use a surgical tool (e.g., a needle driver) to remove a selected suture needle from a suture needle container, and use the surgical tool to pass the selected suture needle through a trocar or tube for delivery at a surgical site.

Figure 19:
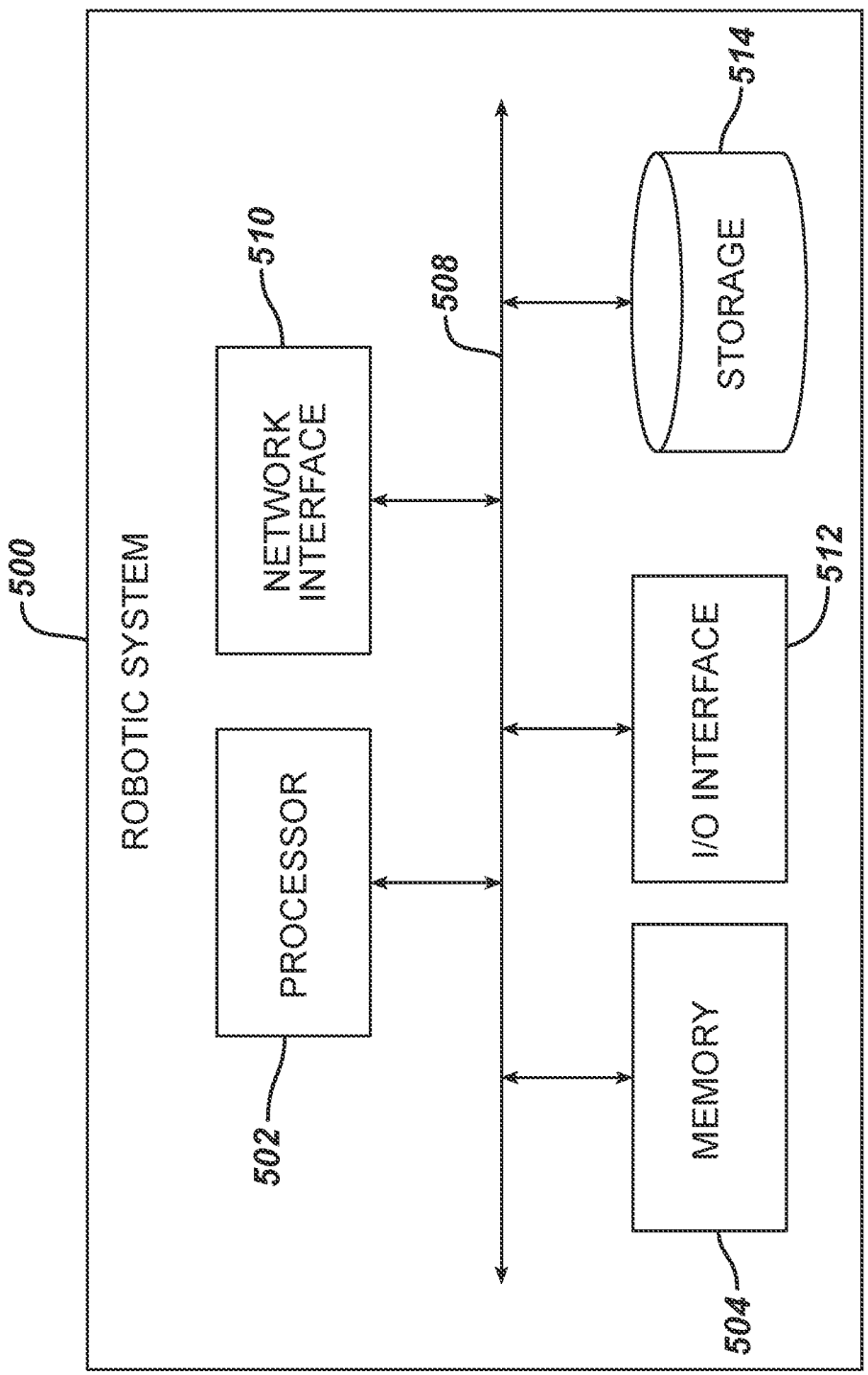
FIG. 19 shows a robotic system for removing a suture needle from a suture needle container and passing the suture needle through a trocar, in accordance with one embodiment of the present patent application.

Referring to FIG. 19, in one embodiment, a robotic system 500 preferably includes one or more processors 502, which can control the operation of the robotic system 500. "Processors" are also referred to herein as "controllers." The processor(s) 502 may include any type of microprocessor or central processing unit (CPU), including programmable general-purpose or special-purpose microprocessors and/or any one of a variety of proprietary or commercially available single or multi-processor systems. The robotic system 500 may also include one or more memory devices 504, which can provide temporary storage for code to be executed by the processor(s) 502 or for data acquired from one or more users, storage devices, and/or databases. The memory device 504 may include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the robotic system 500 may be coupled to a bus system 508. The illustrated bus system 508 is an abstraction that represents any one or more separate physical busses, communication lines/interfaces, and/or multi-drop or point-to-point connections, connected by appropriate bridges, adapters, and/or controllers. The robotic system 500 may also include one or more network interface(s) 510, one or more input/output (IO) interface(s) 512, and one or more storage device(s) 514.

The network interface(s) 512 preferably enable the robotic system 500 to communicate with remote devices, e.g., other computer systems, over a network, and can be, for non-limiting example, remote desktop connection interfaces, Ethernet adapters, and/or other local area network (LAN) adapters. The 10 interface(s) 512 may include one or more interface components to connect the robotic system

500 with other electronic equipment. For non-limiting examples, the IO interface(s) 512 may include high speed data ports, such as universal serial bus (USB) ports, 1394 ports, Wi-Fi, Bluetooth, etc. Additionally, the robotic system 500 may be accessible to a human user, and thus the IO interface(s) 512 can include displays, speakers, keyboards, pointing devices, and/or various other video, audio, or alphanumeric interfaces. The storage device(s) 514 may include any conventional medium for storing data in a non-volatile and/or non-transient manner. The storage device(s) 514 may thus hold data and/or instructions in a persistent state, i.e., the value(s) are retained despite interruption of power to the robotic system 500. The storage device(s) 514 may include one or more hard disk drives, flash drives, USB drives, optical drives, various media cards, diskettes, compact discs, and/or any combination thereof and can be directly connected to the robotic system 500 or remotely connected thereto, such as over a network. In one embodiment, the storage device(s) may include a tangible or non-transitory computer readable medium configured to store data, e.g., a hard disk drive, a flash drive, a USB drive, an optical drive, a media card, a diskette, a compact disc, etc.

The elements illustrated in FIG. 19 may be some or all of the elements of a single physical machine. In addition, not all of the illustrated elements need to be located on or in the same physical machine. Exemplary robotic and computer systems may include conventional desktop computers, workstations, minicomputers, laptop computers, tablet computers, personal digital assistants (PDAs), mobile phones, and the like.

The robotic system 500 may include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language may be in HyperText Markup Language (HTML) or other conventional forms, including embedded Extensible Markup Language (XML), scripts, controls, and so forth. The computer system 500 may also include a web server for generating and/or delivering the web pages to client computer systems.

In one embodiment, the robotic system 500 may be provided as a single unit, e.g., as a single server, as a single tower, contained within a single housing, etc. The single unit may be modular such that various aspects thereof can be swapped in and out as needed for, e.g., upgrade, replacement, maintenance, etc., without interrupting functionality of any other aspects of the system. The single unit may be scalable with the ability to be added to as additional modules and/or additional functionality of existing modules are desired and/or improved upon.

A robotic or computer system may also include any of a variety of other software and/or hardware components, including by way of non-limiting example, operating systems and database management systems. Although an exemplary robotic system is depicted and described herein, it will be appreciated that this is for sake of generality and convenience. In other embodiments, the robotic system may differ in architecture and operation from that shown and described herein.

The systems and devices disclosed herein may also be designed to be disposed of after a single use, or they can be designed to be used multiple times. In either case, however, the systems and devices may be reconditioned for reuse after at least one use. Reconditioning may include any combination of the steps of disassembly of the device, followed by cleaning or replacement of particular pieces and subsequent reassembly. In particular, the systems and devices may be disassembled, and any number of the particular pieces or parts of the systems and devices may be selectively replaced or removed in any combination. Upon cleaning and/or replacement of particular parts, the systems and devices may be reassembled for subsequent use either at a reconditioning facility, or by a surgical team immediately prior to a surgical procedure. Those skilled in the art will appreciate that reconditioning of the systems and devices may utilize a variety of techniques for disassembly, cleaning/replacement, and reassembly. Use of such techniques, and the resulting reconditioned systems and devices, are all within the scope of the present application.

As noted above, in one embodiment, the systems, devices and methods disclosed herein may be used during robotic surgical procedures, such as a hernia repair procedure. In one embodiment, the patient is prepared for surgery by administering anesthesia. In one embodiment, abdominal access may be attained by inserting two or more ports through the abdominal wall and insufflating the abdominal cavity. In one embodiment, a surgical robot is attached to the pre-placed ports. The hernia site may be assessed under direct visualization using a laparoscopic camera. Adhesions are reduced and the peritoneum sac is excised, if appropriate. A mesh is placed into the abdominal cavity. The surgeon selects from a variety of suture implants to identify one appropriate for the type of hernia repair being performed. The variety may include different tissue anchors, total number of tissue anchors on a suture implant, different suture loop lengths, different suture lengths, etc.

The robotic systems disclosed herein may be coupled with an inventory management system for documenting the type of suture needle that has been used and generating reports and/or ordering replacement parts to restock inventory. The robotic systems disclosed herein may be coupled with an invoicing system for charging expenses to accounts (e.g., a patient's account) and generating invoices. The robotic systems disclosed herein track the types of medical procedures that are performed and the types of suture needles that are selected to perform the different types of medical procedures. The robotic systems may provide computer generated reports or alerts to surgeons to "advise" the surgeons of the types of suture needles that are typically used for particular types of surgical procedures and to advise surgeons if the suture needle that has been selected falls outside the range of suture needles normally selected for certain procedures. For example, if a surgeon selected to use a type of suture needle that is rarely or never used for a particular surgical procedure, the robotic system may generate a message to the surgeon to inform the surgeon of that fact. The robotic system may then make a recommendation to the surgeon regarding the type of suture needle that he/she may want to select. Thus, the robotic system may provide real time guidance for a surgeon regarding the proper tools to use for different types of surgical procedures.

As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

In one embodiment, a delivery device, such as a needle driver, secures one of the suture needles from one of the suture needle containers. The distal end of the delivery device is advanced through one of the port openings for delivering the selected suture needle at a surgical site.

In one embodiment, the systems and delivery devices disclosed herein may be coupled with and/or be in communication with a robotic surgical system, such as the systems and devices disclosed in U.S. Pat. No. 9,125,662 to Shelton, the disclosure of which is hereby incorporated by reference herein. In one embodiment, the robotic surgical system may have a sterile barrier located between the applicator instruments and surgical tools and the robotic part of the robotic surgical system, whereby the systems, delivery devices, suture needle containers, suture needles, and sutures are located in the sterile environment.

In one embodiment, a robotic surgical system may have a master controller and control systems such as the systems and devices disclosed in U.S. Pat. No. 7,524,320, the disclosure of which is hereby incorporated by reference herein. The master controller may have control elements (e.g., knobs, actuators) that are engaged by a surgeon and manipulated in space while the surgeon views a surgical site through a video monitor and/or stereo display. The master controller may include manual input devices that move with multiple degrees of freedom. In one embodiment, the master control has an actuator for actuating surgical tools (e.g., loading a surgical needle onto a needle driver).

In one embodiment, the robotic surgical system may include a robotic cart or rack that is configured to actuate a plurality of surgical tools and/or instruments. Various robotic surgery systems and methods employing master controller and robotic cart arrangements are disclosed in U.S. Pat. No. 6,132,368, the disclosure of which is hereby incorporated by reference herein. In one embodiment, a robotic cart or rack may include a base from which surgical tools are supported. In one embodiment, the surgical tools may be supported by a series of manually articulatable linkages, generally referred to as set-up joints, and a robotic manipulator. These structures may have protective covers extending over much of the robotic linkage. The protective covers may be optional, and may be limited in size or entirely eliminated to minimize the inertia that is encountered by servomotors used to manipulate such devices, to limit the volume of moving components so as to avoid collisions, and to limit the overall weight of the robotic cart. In one embodiment, the robotic cart may have dimensions suitable for transporting the cart between operating rooms. The robotic cart is preferably configured to pass through standard operating room doors and onto standard hospital elevators. The robotic cart preferably has a weight and includes one or more wheels that allow the cart to be easily moved and positioned adjacent an operating table.

Other embodiments may incorporate a wide variety of alternative robotic structures, including those described in U.S. Pat. No. 5,878,193, the disclosure of which is hereby incorporated by reference herein. Additionally, while the data communication between a robotic component and the processor of the robotic surgical system is described with reference to communication between the surgical tool and the master controller, similar communication may take place between circuitry of a manipulator, a set-up joint, an endoscope or other image capture device, or the like, and the processor of the robotic surgical system for component compatibility verification, component-type identification, component calibration communication, and confirmation of coupling of the component to the robotic surgical system.

In one embodiment, during a surgical procedure, a surgeon may input control commands to the master controller or a control unit of the robotic surgical system, which "robotically-generates" output motions that are ultimately transferred to the systems, needle drivers, suture needle containers, and/or the delivery devices disclosed herein. As used herein, the terms "robotically-generates" or "robotically-generated" refer to motions that are created by powering and controlling the motors of the robotic surgical system and other power driven components. These terms are distinguishable from the terms "manually-actuatable" or "manually generated," which refer to actions taken by a surgeon that result in control motions that are generated independent from those motions that are generated by powering the motors of the robotic surgical system.

Versions of the devices described above may have application in conventional medical treatments and procedures conducted by a medical professional, as well as application in robotic-assisted medical treatments and procedures. For example, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

In one embodiment, the systems and devices disclosed herein may be sterilized before and/or after a surgical procedure. In one sterilization technique, a suture needle and attached suture are placed inside a suture needle container that is closed and/or sealed by a cover. The cover may be made of various materials used for obtaining and maintaining sterile environments within sealed containers such as foil covers, plastic covers, polymer covers, high-density polyethylenes, and/or covers made of TYVEK sheets. The sealed containers may be placed in a field of radiation that can penetrate the container, such as gamma radiation, x-rays, or high-energy electrons. The radiation may kill bacteria on suture needle containers, suture needles, sutures, and sealing covers. The sterilized containers may be stored in the sterile container for later use. The sealed containers may also be sterilized using any other technique known in the art, including but not limited to beta or gamma radiation, ethylene oxide, or steam.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A surgical method comprising:
    arranging a plurality of suture needle containers in a surgical environment;
    at least one of said suture needle containers comprising a receptacle having a proximal end with an opening and a distal end that is closed by an end wall, a suture needle disposed within said receptacle, and a cover sealing the opening at the proximal end of said receptacle for maintaining a sterile environment for said suture needle inside said receptacle;
    causing a controller of a surgical robotic system to transmit input instructions to an electromechanical tool for breaching said cover for providing access to said suture needle disposed within said receptacle;
    after breaching said cover, using a distal end of a surgical tool for securing said suture needle and removing said secured suture needle from the opening at the proximal end of said receptacle; and
    causing said controller of said surgical robotic system to transmit input instruction to said surgical tool for advancing said secured suture needle through a cannula and delivering said secured suture needle to a surgical site.

2. The method as claimed in claim 1, further comprising:
    using said secured suture needle for performing a surgical procedure at the surgical site;
    after performing the surgical procedure, retracting said secured suture needle through said cannula for removing said secured suture needle from the surgical site.

3. The method as claimed in claim 1, wherein said at least one suture needle container comprises:
    a mandrel located inside said receptacle, said mandrel having a tubular wall that projects from said end wall of said receptacle toward the opening at the proximal end of said receptacle; and
    an elongated slot formed in said tubular wall that extends from a proximal end of said tubular wall toward said end wall of said receptacle.

4. The method as claimed in claim 3, wherein prior to removing said secured suture needle from said receptacle, said secured suture needle is disposed within said elongated slot of said tubular wall with a distal end of said secured suture needle being disposed inside said tubular wall and a proximal end of said secured suture needle being disposed outside said tubular wall.

5. The method as claimed in claim 4, wherein said receptacle further comprises an outer wall that extends between the proximal and distal ends of said receptacle, and wherein prior to removing said secured suture needle from said receptacle, the proximal end of said secured suture needle is located between an outer surface of said tubular wall and an inner surface of said outer wall of said receptacle.

6. The method as claimed in claim 5, further comprising securing a suture to the proximal end of said secured suture needle.

7. The method as claimed in claim 6, further comprising prior to removing said secured suture needle from said opening at the proximal end of said receptacle, winding said suture around said tubular wall.

8. The method as claimed in claim 3, wherein said tubular wall defines a guide channel having a height and a width that is configured to receive the distal end of said surgical tool, said guide channel extending from the proximal end of said tubular wall to said end wall of said receptacle.

9. The method as claimed in claim 1, wherein said cover sealing the opening at the proximal end of said receptacle comprises a material selected from a group consisting of foil, polymers, plastics, and high-density polyethylenes.

10. The method as claimed in claim 1, further comprising storing said suture needle containers on a rack or a surgical table located inside an operating room for use during a surgical procedure.

11. The method as claimed in claim 1, wherein at least two or more of said suture needle containers contain different types of suture needles.

12. The method as claimed in claim 1, wherein one or more of said suture needle containers have cross-sectional shapes selected from the group consisting of circles, triangles, and non-symmetric shapes.

13. The method as claimed in claim 1, wherein each of said suture needle containers comprises a unique identifier that identifies a particular type of suture needle or suture needle/suture thread combination that is disposed inside said suture needle container.

14. A surgical method comprising:
    arranging a plurality of suture needle containers in a surgical environment;
    each said suture needle container comprising a receptacle having a proximal end with an opening and a distal end that is closed by an end wall, a mandrel located inside said receptacle having a tubular wall that projects from said end wall toward the opening at the proximal end of said receptacle, an elongated slot formed in said tubular wall that extends from a proximal end of said tubular wall toward said end wall of said receptacle, a suture needle disposed within said elongated slot having distal end disposed inside said tubular wall and a proximal end disposed outside said tubular wall, and a cover sealing the opening at the proximal end of said receptacle for maintaining a sterile environment inside said receptacle;
    after selecting one of said suture needles that is sealed inside one of said suture needle containers for use, causing a controller on a surgical robotic system to transmit input instructions to an electromechanical surgical tool for breaching said cover of the selected one of said suture needle containers, securing the distal end of the selected one of said suture needles, and removing said secured suture needle from said breached suture needle container; and
    causing said controller of said surgical robotic system to transmit input instructions to said electromechanical surgical tool to advance said secured suture needle through a cannula for delivering said secured suture needle to a surgical site.

15. The method as claimed in claim 14, further comprising:
    using said secured suture needle for performing a surgical procedure at the surgical site; and
    after performing the surgical procedure, retracting said secured suture needle through said cannula for removing said secured suture needle from the surgical site.

16. The method as claimed in claim 14, wherein prior to removing said secured suture needle from said receptacle, said secured suture needle is disposed within said elongated slot of said tubular wall with a distal end of said secured suture needle being disposed inside said tubular wall and a proximal end of said secured suture needle being disposed outside said tubular wall.

17. The method as claimed in claim 16, further comprising prior to removing said secured suture needle from said opening at the proximal end of said receptacle, securing a suture to the proximal end of said secured suture needle, and winding said suture around said tubular wall.

\* \* \* \* \*